US009783567B2

(12) United States Patent
Yu et al.

(10) Patent No.: US 9,783,567 B2
(45) Date of Patent: *Oct. 10, 2017

(54) PROCESSES AND INTERMEDIATES FOR PREPARING ANTI-HIV AGENTS

(71) Applicant: Gilead Sciences, Inc., Foster City, CA (US)

(72) Inventors: Richard Hung Chiu Yu, San Francisco, CA (US); Brandon Heath Brown, Burlingame, CA (US); Richard P. Polniaszek, Menlo Park, CA (US); Benjamin R. Graetz, San Mateo, CA (US); Keiko Sujino, Edmonton (CA); Duong Tran, Edmonton (CA); Alan Scott Triman, Sunnyvale, CA (US); Kenneth M. Kent, Sunnyvale, CA (US); Steven Pfeiffer, Camarillo, CA (US)

(73) Assignee: Gilead Sciences, Inc., Foster City, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/046,399

(22) Filed: Feb. 17, 2016

(65) Prior Publication Data

US 2016/0340379 A1 Nov. 24, 2016

Related U.S. Application Data

(63) Continuation of application No. 14/615,357, filed on Feb. 5, 2015, now Pat. No. 9,296,779, which is a continuation of application No. 13/475,569, filed on May 18, 2012, now Pat. No. 8,987,437.

(60) Provisional application No. 61/488,133, filed on May 19, 2011.

(51) Int. Cl.
| | |
|---|---|
| C07H 19/00 | (2006.01) |
| C07H 19/22 | (2006.01) |
| C07H 19/20 | (2006.01) |
| C07H 19/02 | (2006.01) |
| C07H 19/04 | (2006.01) |
| C07H 19/173 | (2006.01) |
| C07D 473/34 | (2006.01) |
| C07F 9/40 | (2006.01) |
| C07F 9/44 | (2006.01) |
| C07F 9/6561 | (2006.01) |
| C07H 19/16 | (2006.01) |
| C07H 23/00 | (2006.01) |

(52) U.S. Cl.
CPC .......... *C07H 19/20* (2013.01); *C07D 473/34* (2013.01); *C07F 9/4075* (2013.01); *C07F 9/4449* (2013.01); *C07F 9/65616* (2013.01); *C07H 19/02* (2013.01); *C07H 19/04* (2013.01); *C07H 19/16* (2013.01); *C07H 19/173* (2013.01); *C07H 23/00* (2013.01)

(58) Field of Classification Search
None
See application file for complete search history.

(56) References Cited

U.S. PATENT DOCUMENTS

| 4,198,355 | A | 4/1980 | Schmitt |
| 5,459,256 | A | 10/1995 | Marquez et al. |
| 7,390,791 | B2 | 6/2008 | Becker et al. |
| 7,871,991 | B2 | 1/2011 | Boojamra et al. |
| 8,022,083 | B2 | 9/2011 | Boojamra et al. |
| 8,329,926 | B2 | 12/2012 | Boojamra et al. |
| 8,697,861 | B2 | 4/2014 | Boojamra et al. |
| 8,987,437 | B2 | 3/2015 | Yu et al. |
| 9,296,779 | B2 | 3/2016 | Yu et al. |
| 2005/0009043 | A1 | 1/2005 | Becker et al. |
| 2012/0296076 | A1 | 11/2012 | Yu et al. |

FOREIGN PATENT DOCUMENTS

| GB | 835785 A | 5/1960 | |
| WO | WO-02/08241 | 1/2002 | |
| WO | WO-03/090691 | 11/2003 | |
| WO | WO-2006/015261 A2 | 2/2006 | |
| WO | WO-2006/020276 | 2/2006 | |
| WO | WO-2006/110157 | 10/2006 | |
| WO | WO-2007/014352 A2 | 2/2007 | |
| WO | WO 2008/100447 | 8/2008 | |
| WO | WO 2008/100447 A2 * | 8/2008 | .......... C07F 9/65586 |
| WO | WO-2010/005986 A1 | 1/2010 | |
| WO | WO-2011/003018 A2 | 1/2011 | |
| WO | WO-2011/003018 A3 | 1/2011 | |

OTHER PUBLICATIONS

Australian Office Action dated Jan. 27, 2015 for Australian Patent Application No. 2012255029.
Avila et al. (1989). "Phosphonium Ion Fragmentations Relevant to Organophosphonate Biodegradation," *J. Am. Chem. Soc.* 111:8969-8970.
Ballatore, C. et al. (Apr. 23, 2001). "Synthesis and Evaluation of Novel Amidate Prodrugs of PMEA and PMPA," *Bioorganic & Medicinal Chem. Letters* 11(8):1053-1056.
Boojamra, C.G. et al. (Feb. 1, 2008, e-pub. Dec. 5, 2007). "Synthesis and Anti-HIV Activity of GS-9148 (2'-Fd4AP), a Novel Nucleoside Phosphonate HIV Reverse Transcriptase Inhibitor," *Bioorganic & Medicinal Chem. Letters* 18(3):1120-1123.
Cen, Y. et al. (Feb. 2010). "Efficient Syntheses of Clofarabine and Gemcitabine from 2-Deoxyribonolactone," *Nucleosides, Nucleotides and Nucleic Acids* 29(2):113-122.
Chapman, H. et al. (Apr.-Jul. 2001). "Practical Synthesis, Separation, and Stereochemical Assignment of the PMPA Pro-Drug GS-7340," *Nucleosides, Nucleotides & Nucleic Acids* 20(4-7):621-628.
Fry et al. (1984). "Alkylations Using Methyltrialkoxyphosphonium Tetrafluoborate Salts. Synthetic and Mechanistic Aspects of Methyl, Ethyl, 2-Propyl, and 2-Octyl Group Transfers," *J. Org. Chem.* 49:4877-4880.

(Continued)

*Primary Examiner* — Patrick Lewis
(74) *Attorney, Agent, or Firm* — Gilead Sciences, Inc.

(57) ABSTRACT

The invention provides synthetic processes and synthetic intermediates that can be used to prepare compounds having useful anti-HIV properties.

5 Claims, No Drawings

(56) References Cited

OTHER PUBLICATIONS

Hersh et al. (Mar. 19, 2004). "Synthesis and Structural Characterization of Trivalent Amino Acid Derived Chiral Phosphorus Compounds," *J. Org. Chem.* 69(6):2153-2163.
International Search Report mailed on Jul. 20, 2012 for PCT Patent Application No. PCT/US2012/038615 filed on May 18, 2012, 6 pages.
Japanese Office Action issued Oct. 16, 2015 for Japanese Appl. No. 2014-511589.
Kielbasinski et al. (1998). "Lipase-Promoted Kinetic Resolution of Racemic, P-Chiral Hydroxymethylphosphonates and Phosphinates," Tetrahedron: Asymmetry 9:3283-3287.
New Zealand Office Action mailed on Aug. 20, 2014, for New Zealand Patent Application No. 618939, filed on May 18, 2012, 2 pages.
Notice of Allowance mailed on Nov. 7, 2014, for U.S. Appl. No. 13/475,569, filed May 18, 2012, 5 pages.
Notice of Allowance mailed on Aug. 29, 2014, for U.S. Appl. No. 13/475,569, filed May 18, 2012, 8 pages.
Ray, A.S. et al. (Feb. 2008; e-pub. Dec. 3, 2007). "Intracellular Metabolism of the Nucleotide Prodrug GS-9131, a Potent Anti-Human Immunodeficiency Virus Agent," *Antimicrob. Agents Chemother.* 52(2):648-654.
Written Opinion of the International Searching Authority mailed on Jul. 20, 2012 for PCT Patent Application No. PCT/US2012/038615 filed on May 18, 2012, 8 pages.
Cihlar et al (2009) "Novel Nucleotide Human Immunodeficiency Virus Reverse Transcriptase Inhibitor GS-9148 with a Low Nephrotoxic Potential: Characterization of Renal Transport and Accumulation" Antimicrob Agents Chemother; vol. 53(1):150-156.
LaFlamme et al. (2007) "Novel 2'-Fluoro Substituted Nucleotide HIV Reverse Transcriptase Inhibitor GS-9148 Exhibits Low Potential for Mitochondrial Toxicity In Vitro" *47th Interscience Conference on Antimicrobial Agents and Chemotherapy*; Chicago.
Office Action mailed Oct. 25, 2016 for EP Application No. 12725570.1.
Office Action mailed Nov. 18, 2016 for JP Application No. 2016-005955.
Australian Examination Report mailed Feb. 2, 2017 for AU Application No. 2016208292, filed Jul. 26, 2016.

\* cited by examiner

PROCESSES AND INTERMEDIATES FOR PREPARING ANTI-HIV AGENTS

CROSS REFERENCE TO RELATED APPLICATION

This patent application is a continuation of U.S. patent Application Ser. No. 14/615,357, filed Feb. 5, 2015, which is a continuation of U.S. patent Application Ser. No. 13/475,569, filed May 18, 2012, which claims the benefit of priority of U.S. Provisional Patent Application Ser. No. 61/488,133, filed May 19, 2011. The contents of each application is incorporated by reference.

BACKGROUND OF THE INVENTION

International Patent Application Publication Number WO 2006/110157 and International Patent Application Publication Number WO 2006/015261 provide phosphonamidate derivatives of (2R',5R')-9-(3-fluoro-2,5-dihydro-5-phosphonomethoxy-2-furanyl)adenine that are reported to be useful as anti-HIV agents. Compound 13 is one such derivative.

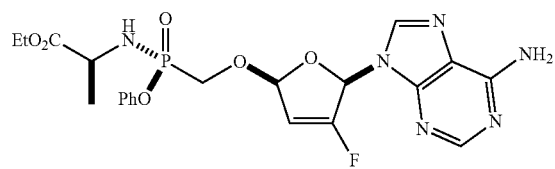

13

International Patent Application Publication Number WO 2010/005986 provides salt forms of compound 13 including the citrate salt (compound 14) which are also reported to be useful as anti-HIV agents.

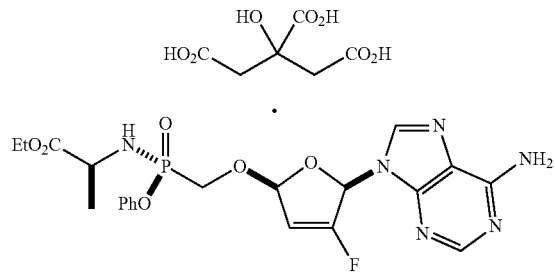

14

There is currently a need for improved methods for preparing certain compounds reported in International Patent Application Publication Numbers WO 2006/110157, WO 2006/015261 and WO 2010/005986. In particular, there is a need for new synthetic methods that are simpler or less expensive to carry out, that provide an increased yield, or that eliminate the use of toxic or costly reagents.

SUMMARY OF THE INVENTION

The present invention provides new synthetic processes and synthetic intermediates that are useful for preparing the compound of formula 13 or salts or stereoisomers thereof. The present invention also provides new synthetic processes and synthetic intermediates that are useful for preparing additional compounds reported in International Patent Application Publication Numbers WO 2006/110157, WO 2006/015261, WO 2010/005986, WO2002008241 and U.S. Pat. No. 7,390,791.

Accordingly, in one embodiment, the invention provides a method for preparing a compound of formula 13b:

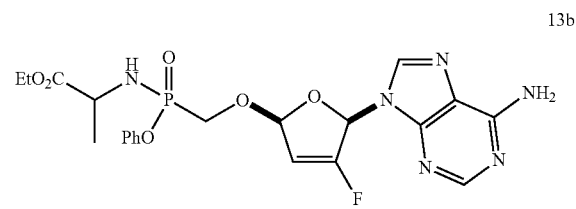

13b or a salt thereof, comprising converting a compound of formula 12b:

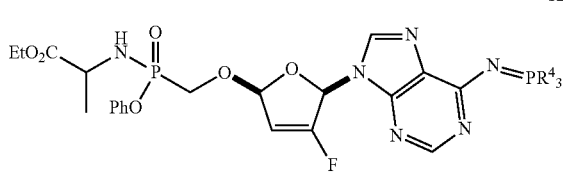

12b or a salt thereof, to the compound of formula 13b or the salt thereof, wherein each $R^4$ is independently $(C_1-C_6)$alkyl, $(C_3-C_7)$cycloalkyl or aryl, wherein any $(C_3-C_7)$cycloalkyl or aryl is optionally substituted with one or more (e.g. 1, 2 or 3) $(C_1-C_6)$alkyl groups.

In another embodiment the invention provides a method of preparing a compound of formula 4a:

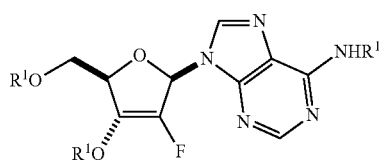

4a or a salt thereof, comprising reacting a corresponding compound of formula 2a:

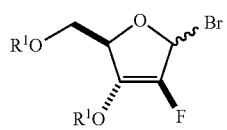

2a with a corresponding compound of formula 3a:

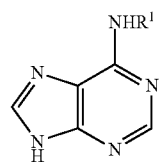

3a or a salt thereof, to provide the compound of formula 4a or the salt thereof, wherein each $R^1$ is independently —C(═O)(C$_1$-C$_6$)alkyl, —C(═O)(C$_3$-C$_7$)cycloalkyl or —C(═O)aryl, wherein —C(═O)(C$_3$-C$_7$)cycloalkyl or —C(═)aryl is optionally substituted with one or more (e.g. 1, 2 or 3) (C$_1$-C$_6$)alkyl groups; and provided the compound of formula 3a is not a sodium salt of 3a when the $R^1$ group of the compound of formula 3a is benzoyl.

In another embodiment the invention provides a method of preparing a compound of formula 5a:

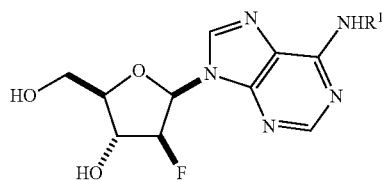

5a or a salt thereof, comprising converting a corresponding compound of formula 4a:

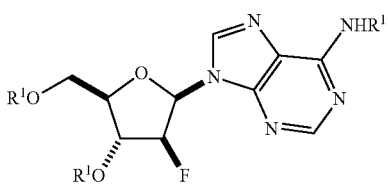

4a or a salt thereof, to the compound of formula 5a or the salt thereof, wherein each $R^1$ is independently —C(═O)(C$_1$-C$_6$)alkyl, —C(═O)(C$_3$-C$_7$)cycloalkyl or —C(═O)aryl, wherein —C(═O)aryl or —C(═O)(C$_3$-C$_7$)cycloalkyl is optionally substituted with one or more (e.g. 1, 2 or 3) (C$_1$-C$_6$)alkyl groups.

In another embodiment the invention provides a method of preparing a compound of formula 7a:

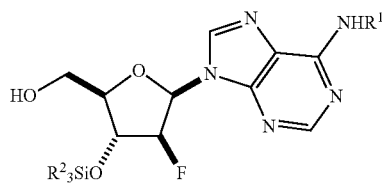

7a or a salt thereof, comprising converting a corresponding compound of formula 5a:

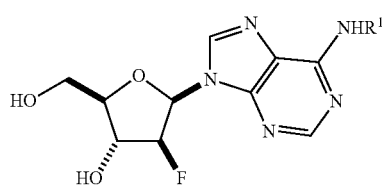

5a or a salt thereof, to the compound of formula 7a or the salt thereof, wherein $R^1$ is —C(═O)(C$_1$-C$_6$)alkyl, —C(═O)(C$_3$-C$_7$)cycloalkyl or —C(═O)aryl, wherein —C(═O)(C$_3$-C$_7$)cycloalkyl or —C(═O)aryl is optionally substituted with one or more (e.g. 1, 2 or 3) (C$_1$-C$_6$)alkyl groups; and each $R^2$ is independently aryl or (C$_1$-C$_6$)alkyl, wherein aryl is optionally substituted with one or more (e.g. 1, 2 or 3) (C$_1$-C$_6$)alkyl groups.

In another embodiment the invention provides a method of preparing a compound of formula 9:

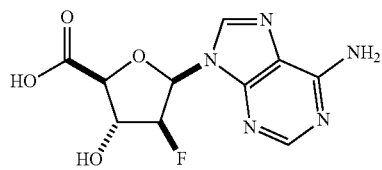

9 or a salt thereof, comprising converting a compound of formula 7a:

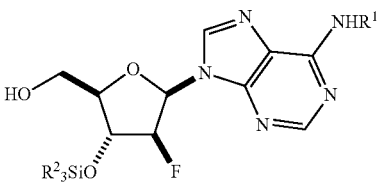

7a or a salt thereof, to the compound of formula 9 or the salt thereof, wherein $R^1$ is —C(═O)(C$_1$-C$_6$)alkyl, —C(═O)(C$_3$-C$_7$)cycloalkyl or —C(═O)aryl, wherein —C(═O)aryl or —C(═O)(C$_3$-C$_7$)cycloalkyl is optionally substituted with one or more (e.g. 1, 2 or 3) (C$_1$-C$_6$)alkyl groups; and each $R^2$ is independently aryl or (C$_1$-C$_6$)alkyl, wherein aryl is optionally substituted with one or more (e.g. 1, 2 or 3) (C$_1$-C$_6$)alkyl groups.

In another embodiment the invention provides a method of preparing a compound of formula 10a:

10a or a salt thereof, comprising converting a compound of formula 9:

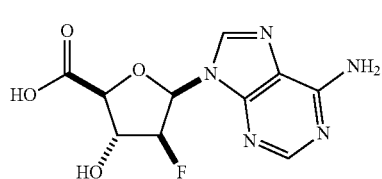

9 or a salt thereof, to the compound of formula 10a or the salt thereof, wherein each $R^4$ is independently (C$_1$-C$_6$)alkyl, ($C_3$-$C_7$)cycloalkyl or aryl, wherein aryl or ($C_3$-$C_7$)cycloalkyl is optionally substituted with one or more (e.g. 1, 2 or 3) ($C_1$-$C_6$)alkyl groups.

In another embodiment the invention provides a method of preparing a compound of formula 11b:

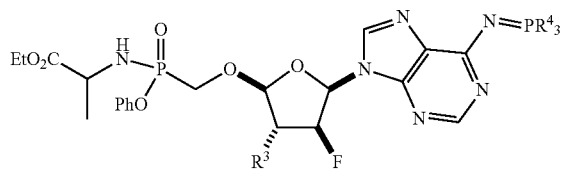

11b or a salt thereof, comprising converting a corresponding compound of formula 10a:

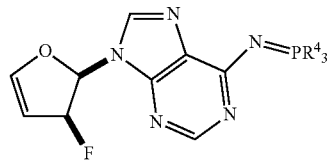

10a or a salt thereof, to the compound of formula 11b or the salt thereof, wherein $R^3$ is I, $R^5$Se or $R^5$S and each $R^4$ and $R^5$ is independently ($C_1$-$C_6$)alkyl, ($C_3$-$C_7$)cycloalkyl or aryl, wherein aryl or ($C_3$-$C_7$)cycloalkyl is optionally substituted with one or more (e.g. 1, 2 or 3) ($C_1$-$C_6$)alkyl groups.

In another embodiment the invention provides a method of preparing a compound of formula 12b:

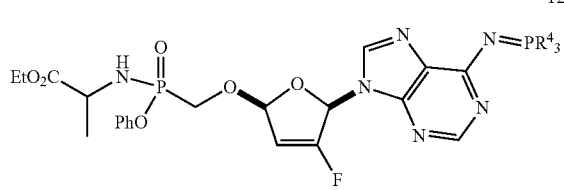

12b or a salt thereof, comprising converting a corresponding compound of formula 11b:

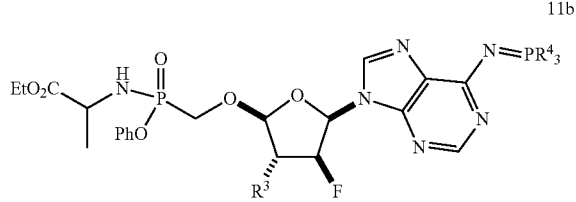

11b or a salt thereof, to the compound of formula 12b or the salt thereof, wherein $R^3$ is I, $R^5$Se or $R^5$S and each $R^4$ and $R^5$ is independently ($C_3$-$C_6$)alkyl, ($C_3$-$C_7$)cycloalkyl or aryl, wherein aryl or ($C_3$-$C_7$)cycloalkyl is optionally substituted with one or more (e.g. 1, 2 or 3) ($C_1$-$C_6$)alkyl groups.

In another embodiment the invention provides a method of preparing a compound of formula 16:

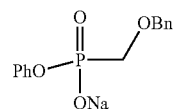

16 comprising converting a compound of formula 15:

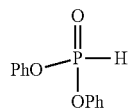

15 to the compound of formula 16, wherein Bn is optionally substituted with one or more (e.g. 1, 2 or 3) groups selected from ($C_1$-$C_6$)alkyl and —O($C_1$-$C_6$)alkyl.

In one embodiment the invention provides a method of preparing a compound of formula 18b:

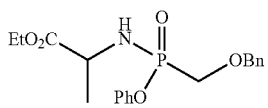

18b comprising converting a corresponding compound of formula 16:

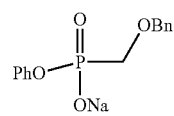

16 to the compound of formula 18b, wherein Bn is optionally substituted with one or more (e.g. 1, 2 or 3) groups selected from ($C_1$-$C_6$)alkyl and —O($C_1$-$C_6$)alkyl.

In another embodiment the invention provides a method of preparing a compound of formula 19b:

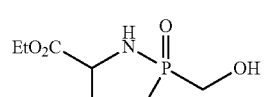

19b comprising converting a compound of formula 18b:

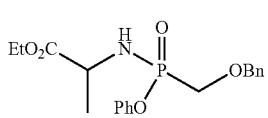

18b to the compound of formula 19b, wherein Bn is optionally substituted with one or more (e.g. 1, 2 or 3) groups selected from ($C_1$-$C_6$)alkyl and —O($C_1$-$C_6$)alkyl.

In another embodiment the invention provides a compound selected from:

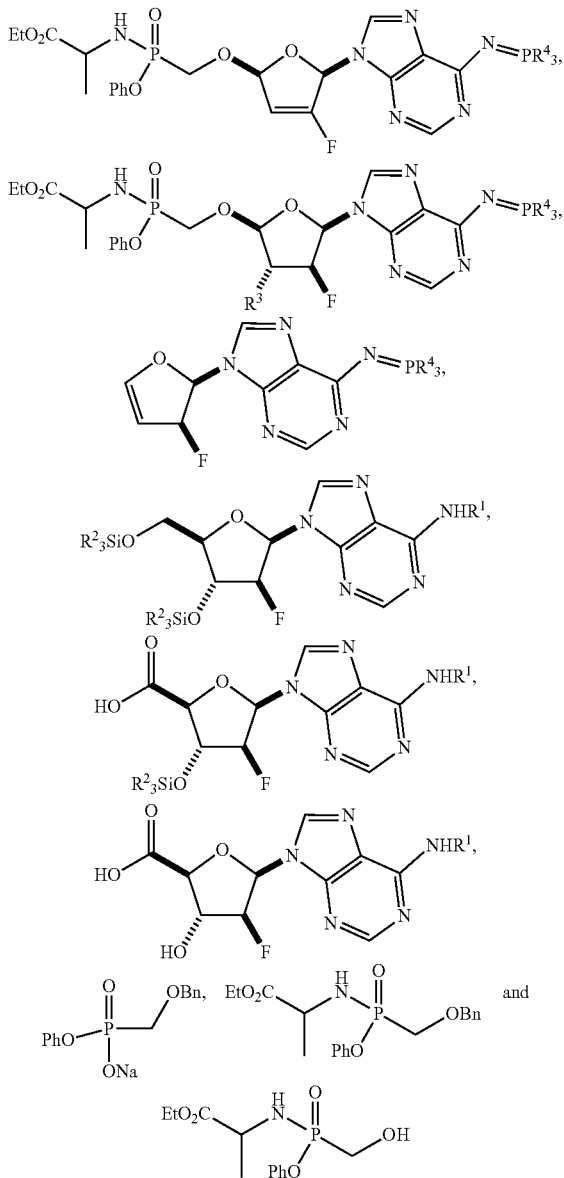

wherein:

Bn is optionally substituted with one or more (e.g. 1, 2 or 3) groups selected from $(C_1\text{-}C_6)$alkyl and $-O(C_1\text{-}C_6)$alkyl;

each $R^1$ is independently $-C(=O)(C_1\text{-}C_6)$alkyl, $-C(=O)(C_3\text{-}C_7)$cycloalkyl or $-C(=O)$aryl, wherein $-C(=O)(C_3\text{-}C_7)$cycloalkyl or $-C(=O)$aryl is optionally substituted with one or more (e.g. 1, 2, 3, 4 or 5) $(C_1\text{-}C_6)$alkyl groups;

each $R^2$ is independently aryl or $(C_1\text{-}C_6)$alkyl, wherein aryl is optionally substituted with one or more (e.g. 1, 2, 3, 4 or 5) $(C_1\text{-}C_6)$alkyl groups;

$R^3$ is I, $R^5$Se or $R^5$S;

Each $R^4$ is independently $(C_1\text{-}C_6)$alkyl, $(C_3\text{-}C_7)$cycloalkyl or aryl, wherein aryl or $(C_3\text{-}C_7)$cycloalkyl is optionally substituted with one or more (e.g. 1, 2, 3, 4 or 5) $(C_1\text{-}C_6)$alkyl groups; and each $R^5$ is independently $(C_1\text{-}C_6)$alkyl, $(C_3\text{-}C_7)$cycloalkyl or aryl, wherein aryl or $(C_3\text{-}C_7)$cycloalkyl is optionally substituted with one or more (e.g. 1, 2, 3, 4 or 5) $(C_1\text{-}C_6)$alkyl groups;

and salts thereof, which compounds are useful intermediates for preparing the compounds of formula 13 or 13b or salts or stereoisomers thereof.

The invention also provides additional synthetic processes disclosed herein that are useful for preparing the compounds of formula 13 and formula 13b as well as salts or stereoisomers thereof.

The methods and intermediates described in the summary of the invention and herein below, which are useful for preparing the compound of formula 13 or a salt thereof or the compounds of formula 13b or salts thereof, represent a significant improvement over previous methods. For example, the previously reported methods for the synthesis of the compounds of formula 13 required a late stage amination of a methoxy purine to provide the corresponding amino purine which may introduce higher levels of undesirable side products. This process led to lower overall yields of the final compound. The methods of the current invention avoid this undesirable step as the amine functionality is introduced as part of the purine core from the beginning of the synthesis. Previously reported methods also required the isolation of the compound of formula 13 from a mixture of diastereomers by chiral chromatography. This method of resolution is costly as specialized equipment and significant amounts of production time and labor are needed to effectively remove the undesired compound (e.g. about 50%) from the product mixture. Additionally, the use of this method of resolution of diastereomers in the final stage of a synthetic process is inherently inefficient and undesirable because the overall process transformation yield (i.e. maximum 50%) is severely impacted. The present synthesis does not require such an isolation step as the synthesis described herein utilizes a selected, stereo-defined chiral phosphonamidate (e.g. compound 19) that provides compound 13 as a single diasteromer. In addition, literature methods for the synthesis of compound 4a from compound 1a and 3a (wherein all of the protecting groups are benzoyl) utilized the sodium salt of compound 3a. In contrast, the present invention describes the synthesis of compound of 4a from compound 3a which does not utilize the sodium salt of compound 3a. This modification results in a significantly higher anomeric β/α ratio and thus higher yields. Accordingly, the present invention provides improved methods and intermediates for preparing compound 13 and compounds of formula 13b.

DETAILED DESCRIPTION

The following definitions are used, unless otherwise described:

The term "halo" or "halogen" refers to fluoro, chloro, bromo, or iodo.

The term "alkyl" denotes both straight and branched groups, but reference to an individual radical such as propyl embraces only the straight chain radical, a branched chain isomer such as isopropyl (e.g. iPr or $^i$Pr) being specifically referred to. The term "$(C_1\text{-}C_6)$alkyl" refers to an alkyl of 1-6 carbon atoms.

The term "Bz" as used herein refers to a $-C(=O)$Ph group.

The term "Bn" as used herein refers to a benzyl (i.e. CH$_2$phenyl) group.

The term "aryl" as used herein refers to a ring structure of from 6 to 14 carbon atoms in the ring. Aryl includes a single aromatic ring (e.g. phenyl). Aryl also includes multiple condensed rings (e.g. bicyclic or multicyclic rings such as naphthyl or anthryl) wherein the condensed rings may be aromatic, saturated or partially saturated, provided that at least one of the condensed rings is aromatic. Such multiple condensed rings may be optionally substituted with one or more (e.g. 1, 2 or 3) oxo groups on any non-aromatic portion (i.e. saturated or partially unsaturated) of the multiple condensed ring. It is to be understood that the point(s) of attachment of a bicyclic or multicyclic aryl can be at any position of the ring system including an aromatic or non-aromatic portion of the ring. Exemplary aryls include, but are not limited to phenyl, indanyl, naphythyl, 1,2-dihydronaphthyl and 1,2,3,4-tetrahydronaphthyl.

The term "heteroaryl" as used herein refers to a ring structure of from 1 to 10 carbon atoms and 1 to 4 heteroatoms selected from the group consisting of oxygen, nitrogen and sulfur in the ring. The sulfur and nitrogen heteroatoms atoms may also be present in their oxidized forms. Heteroaryl includes a single aromatic ring with at least one heteroatom (e.g. pryridyl, pyrimidinyl or furyl). Heteroaryl also includes multiple condensed rings (e.g. bicyclic or multicyclic rings such as indolizinyl or benzothienyl) wherein the condensed rings may or may not be aromatic and/or contain a heteroatom provided that at least one of the condensed rings is aromatic with at least one heteroatom. Such multiple condensed rings may be optionally substituted with one or more (e.g. 1, 2 or 3) oxo groups on any non-aromatic (i.e. saturated or partially unsaturated) portion of the condensed rings. It is to be understood that the point(s) of attachment of a bicyclic or multicyclic heteroaryl can be at any position of the ring system including an aromatic or non-aromatic portion of the ring. Exemplary heteroaryl groups include, but are not limited to pyridyl, pyrrolyl, pyrazinyl, pyrimidinyl, pyridazinyl, pyrazolyl, thienyl, indolyl, thiophenyl, imidazolyl, oxazolyl, thiazolyl, furyl, oxadiazolyl, thiadiazolyl, quinolyl, isoquinolyl, benzothiazolyl, benzoxazolyl, indazolyl, indolyl, quinoxalyl, quinazolyl, 5,6,7,8-tetrahydroisoquinoline and the like.

The term "cycloalkyl" as used herein refers to a saturated or partially unsaturated cyclic hydrocarbon ring systems, such as those containing 1 or 3 rings and 3 to 8 carbons per ring wherein multiple ring cycloalkyls can have fused, spiro bonds or bridging bonds. Exemplary groups include but are not limited to cyclopropyl, cyclobutyl, cyclopentyl, cyclohexyl, cycloheptyl, cyclooetyl, cyclobutenyl, cyclohexenyl, cyclooetadienyl, decahydronaphthalene and spiro[4,5]decan. The term "$(C_3-C_7)$cycloalkyl" as used herein refers to a saturated or partially unsaturated cyclic hydrocarbon ring having from 3 to 7 carbon atoms in the ring.

The term "haloalkyl" as used herein refers to an alkyl as described above wherein one or more of the hydrogens of the alkyl is replaced with a halogen. The term "$(C_1-C_6)$ haloalkyl" as used herein refers to alkyl groups having from 1 to 6 carbon atoms which are straight or branched wherein at least one and up to all of the hydrogens of the alkyl have been replaced with a halogen.

The term "amino acid" comprises the residues of the natural amino acids including Ala, Gln, Gly, Ile, Leu, Met, Phe, Thr and Val in D or L form. The term also comprises natural and unnatural amino acids protected at the carboxy terminus (e.g. as a $(C_1-C_{10})$alkyl, $(C_3-C_7)$cycloalkyl, —$(C_1-C_6)$alkyl$(C_3-C_7)$cycloalkyl, —$(C_1-C_6)$alkylaryl or aryl ester). Other suitable amino and carboxy protecting groups are known to those skilled in the art (See for example, T. W. Green, *Protecting Groups in Organic Synthesis*: Wiley: New York, 1981, and references cited therein).

In one embodiment the term "amino acid" includes a compound of the following formula:

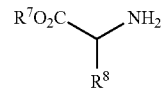

wherein $R^7$ is $(C_1-C_{10})$alkyl, $(C_3-C_7)$cycloalkyl, $(C_3-C_7)$ cycloalkyl$(C_1-C_6)$alkyl-, aryl$(C_1-C_6)$alkyl- or aryl; and $R^8$ is an amino acid sidechain, or a salt thereof.

The term "amino acid sidechain" refers to a moiety that is connected to the backbone of an "amino acid" as described above. For example, the amino acid sidechain of alanine (Ala) is methyl, the amino acid sidechain of phenylalanine (Phe) is benzyl (Bn) and the amino acid sidechain of glycine (Gly) is H. Accordingly, the term "amino acid sidechain" includes but is not limited to the sidechains of the residues of the natural amino including Ala, Gln, Gly, Ile, Leu, Met, Phe, Thr, and Val in D or L form.

In one embodiment the term "amino acid sidechain" includes:

H, $(C_1-C_6)$alkyl, $(C_3-C_7)$cycloalkyl, aryl, heteroaryl, aryl $(C_1-C_6)$alkyl-, heteroaryl$(C_1-C_6)$alkyl- or $(C_3-C_7)$cycloalkyl $(C_1-C_6)$alkyl-, wherein any $(C_1-C_6)$alkyl, $(C_3-C_7)$cycloalkyl, aryl, heteroaryl, aryl$(C_1-C_6)$alkyl-, heteroaryl$(C_1-C_6)$alkyl- or $(C_3-C_7)$cycloalkyl$(C_1-C_6)$alkyl- is optionally substituted with one or more (e.g. 1, 2, 3, 4 or 5) groups selected from, oxo, $(C_1-C_6)$alkyl, —$OR_a$, —$OC(O)R_b$, —$OC(O)NR_cR_d$, —$C(O)R_a$, —$C(O)OR_a$ and —$C(O)NR_cR_d$;

each $R_a$ is independently $(C_1-C_6)$alkyl, $(C_2-C_6)$alkenyl, cycloalkyl, heterocycle, heteroaryl or aryl;

each $R_b$ is independently $(C_1-C_6)$alkyl, $(C_2-C_6)$alkenyl, cycloalkyl, heterocycle, heteroaryl or aryl; and $R_c$ and $R_d$ are each independently selected from H, $(C_1-C_6)$alkyl, $(C_2-C_6)$alkenyl, cycloalkyl, heterocycle, aryl and heteroaryl; or $R_c$ and $R_d$ together with the nitrogen to which they are attached form a pyrrolidino, piperidino, piperazino, azetidino, morpholino, or thiomorpholino.

The term "leaving group" includes any group that can be displaced by a nucleophile (e.g. hydroxy or a deprotonated hydroxy), for example, to form an oxygen-carbon bond. In one embodiment the leaving group is halo or —$OS(O)_2R^L$, where $R^L$ is $(C_1-C_6)$alkyl or aryl, wherein $(C_1-C_6)$alkyl is optionally substituted with one or more halogen, and wherein aryl is optionally substituted with one or more halogen, $(C_1-C_6)$alkyl or $NO_2$.

It will be appreciated by those skilled in the art that a compound having a chiral center may exist in and be isolated in optically active an racemic forms. Some compounds may exhibit polymorphism. It is to be understood that the present invention encompasses processes for preparing any racemic, diastereomeric, optically-active, polymorphic, tautomeric, or stereoisomeric form, or mixtures thereof, of a compound described herein, it being well known in the art how to prepare optically active forms (for example, by resolution of the racemic form by recrystallization techniques, by synthesis from optically-active starting materials, by chiral synthesis, or by chromatographic separation using a chiral stationary phase).

It is to be understood that compounds depicted herein (e.g. either individual compounds or groups of compounds, each either as compositions or as compounds of methods)

may or may not be shown with absolute stereochemistry. If a compound is drawn with stereochemical bonds (e.g. bold, bold-wedge, dashed or dashed-wedge) it is meant to be the specific stereoisomer shown (e.g. diasteromer or enantiomer). Accordingly, wherein applicable, in one embodiment the stereoisomer of a compound depicted herein is about >99% enriched in that stereoisomer. In another embodiment the stereoisomer of a compound depicted herein is about >98% enriched in that stereoisomer. In another embodiment the stereoisomer of a compound depicted herein is about >95% enriched in that stereoisomer. In another embodiment the stereoisomer of a compound depicted herein is about <90% enriched in that stereoisomer. In another embodiment the stereoisomer of a compound depicted herein is about >80% enriched in that stereoisomer. In another embodiment the stereoisomer of a compound depicted herein is about >70% enriched in that stereoisomer. In another embodiment the stereoisomer of a compound depicted herein is about >60% enriched in that stereoisomer. In another embodiment the stereoisomer of a compound depicted herein is about 50% enriched in that stereoisomer.

It is also to be understood that for certain compounds, the bonds, or a portion of the bonds therein, may not have stereochemistry depicted in the chemical structure. For example, for compound 13b:

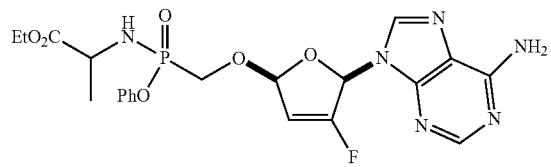

13b the moiety represented by the following structure:

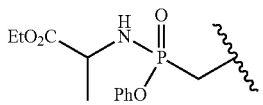

includes all possible stereochemical combinations for this fragment. Thus, the invention includes molecules wherein this fragment is:

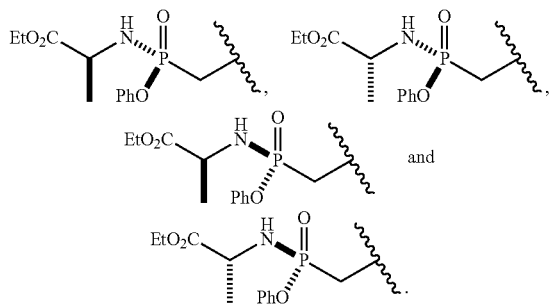

The invention also includes combination of molecules that result from mixtures of any of these isomeric forms.

Specific and preferred values listed below for radicals, substituents, and ranges, are for illustration only; they do not exclude other defined values or other values within defined ranges for the radicals and substituents.

Specifically, $(C_1-C_6)$alkyl can be methyl, ethyl, propyl, isopropyl, butyl, iso-butyl, sec-butyl, pentyl, 3-pentyl, or hexyl.

Specifically, $(C_3-C_7)$cycloalkyl can be cyclopropyl, cyclobutyl, cyclopentyl, cyclohexyl or cycloheptyl.

A specific value for $R^1$ is benzoyl.

A specific value for $R^2$ is ethyl.

A specific value for $R^3$ is I.

A specific value for $R^4$ is phenyl.

A specific value for Bn is phenylCH$_2$—.

Another specific value for $R^2$ is $(C_1-C_6)$alkyl.

Another specific value for $R^1$ is —C(=O)aryl, wherein —C(=O)aryl is optionally substituted with one or more $(C_1-C_6)$alkyl groups.

In one embodiment, the invention provides a method for preparing a compound of formula 13:

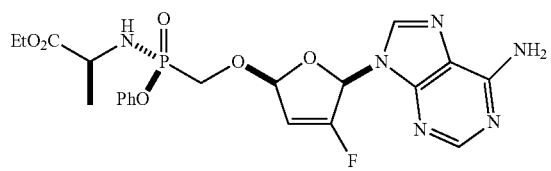

13 or a salt thereof, comprising converting a corresponding compound of formula 12a:

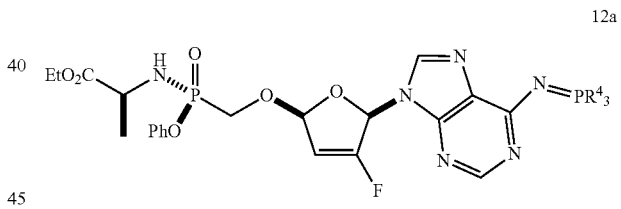

12a or a salt thereof, to the compound of formula 13 or the salt thereof, wherein each $R^4$ is independently $(C_1-C_6)$alkyl, $(C_3-C_7)$cycloalkyl or aryl, wherein any $(C_3-C_7)$cycloalkyl or aryl is optionally substituted with one or more $(C_1-C_6)$alkyl groups.

In one embodiment, the invention provides a method for preparing a compound of formula 13b:

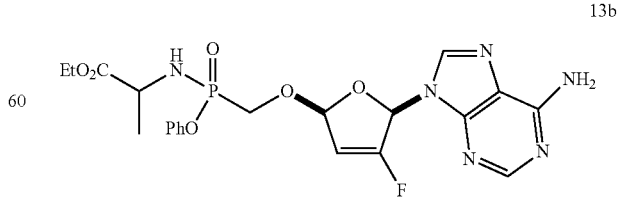

13b or a salt thereof, comprising converting a compound of formula 11b:

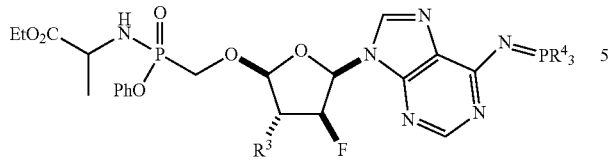

11b or a salt thereof, to the compound of formula 13b or the salt thereof, wherein $R^3$ is I, $R^5Se$ or $R^5S$ and each $R^4$ and $R^5$ is independently $(C_1-C_6)$alkyl, $(C_3-C_7)$cycloalkyl or aryl, wherein aryl or $(C_3-C_7)$cycloalkyl is optionally substituted with one or more (e.g. 1, 2 or 3) $(C_1-C_6)$alkyl groups. In a similar manner the invention provides a method for preparing a compound of formula 13 or a salt thereof, comprising converting a compound of formula 11a or a salt thereof, to the compound of formula 13 or the salt thereof.

In one embodiment, the invention provides a method for preparing a compound of formula 13b:

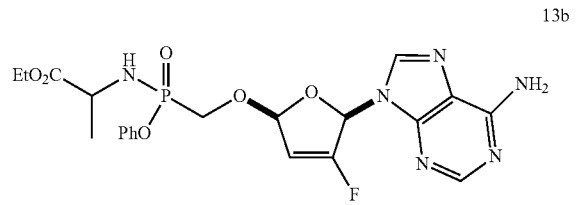

13b or a salt thereof, comprising converting a compound of formula 10a:

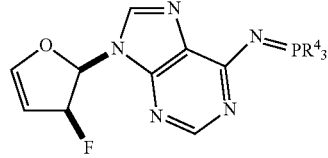

10a or a salt thereof, to the compound of formula 13b or the salt thereof, wherein each $R^4$ is independently $(C_1-C_6)$alkyl, $(C_3-C_7)$cycloalkyl or aryl, wherein aryl or $(C_3-C_7)$cycloalkyl is optionally substituted with one or more (e.g. 1, 2 or 3) $(C_1-C_6)$alkyl groups. In a similar manner the invention provides a method for preparing a compound of formula 13 or a salt thereof, comprising converting a compound of formula 10a or a salt thereof, to the compound of formula 13 or the salt thereof.

In one embodiment, the invention provides a method for preparing a compound of formula 13b:

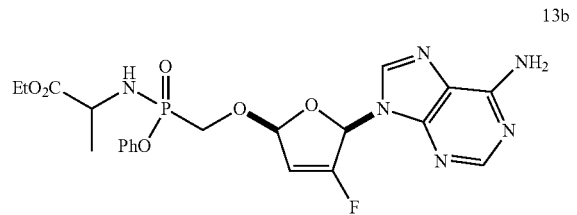

13b or a salt thereof, comprising converting a compound of formula 9:

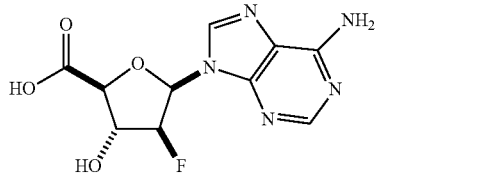

9 or a salt thereof, to the compound of formula 13b or the salt thereof. In a similar manner the invention provides a method for preparing a compound of formula 13 or a salt thereof, comprising converting a compound of formula 9 or a salt thereof, to the compound of formula 13 or the salt thereof.

In one embodiment, the invention provides a method for preparing a compound of formula 13b:

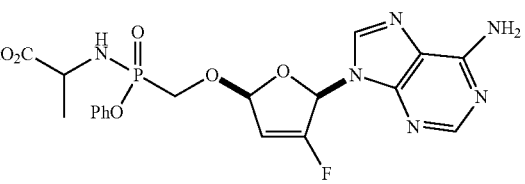

13b or a salt thereof, comprising converting a compound of formula 7a:

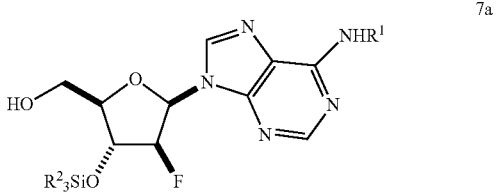

7a or a salt thereof, to the compound of formula 13b or the salt thereof, wherein $R^1$ is —C(=O)$(C_1-C_6)$alkyl, —C(=O)$(C_3-C_7)$cycloalkyl or —C(=O)aryl, wherein —C(=O)aryl or —C(=O)$(C_3-C_7)$cycloalkyl is optionally substituted with one or more (e.g. 1, 2 or 3) $(C_1-C_6)$alkyl groups; and each $R^2$ is independently aryl or $(C_1-C_6)$alkyl, wherein aryl is optionally substituted with one or more (e.g. 1, 2 or 3) $(C_1-C_6)$alkyl groups. In a similar manner the invention provides a method for preparing a compound of formula 13 or a salt thereof, comprising converting a compound of formula 7a or a salt thereof, to the compound of formula 13 or the salt thereof.

In one embodiment, the invention provides a method for preparing a compound of formula 13b:

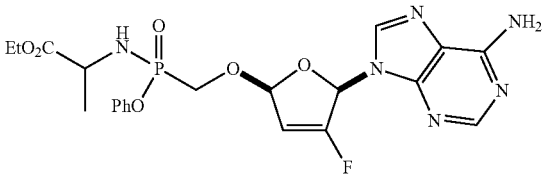

13b or a salt thereof, comprising converting a compound of formula 5a:

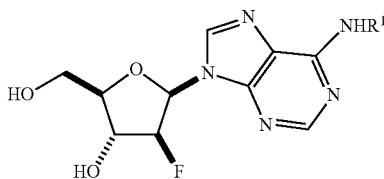

5a or a salt thereof, to the compound of formula 13b or the salt thereof, wherein R¹ is —C(=O)(C₁-C₆)alkyl, —C(=O)(C₃-C₇)cycloalkyl or —C(=O)aryl, wherein —C(=O)(C₃-C₇)cycloalkyl or —C(=O)aryl is optionally substituted with one or more (e.g. 1, 2 or 3) (C₁-C₆)alkyl groups. In a similar manner the invention provides a method for preparing a compound of formula 13 or a salt thereof, comprising converting a compound of formula 5a or a salt thereof, to the compound of formula 13 or the salt thereof.

In one embodiment, the invention provides a method for preparing a compound of formula 13b:

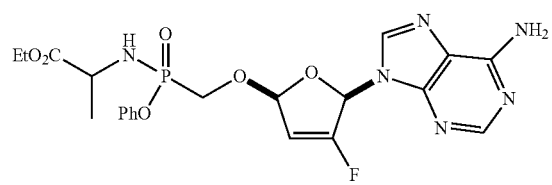

13b or a salt thereof, comprising converting a compound of formula 4a:

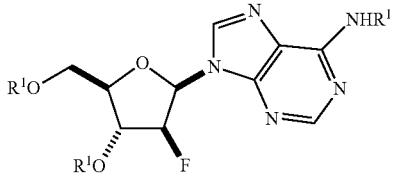

4a or a salt thereof, to the compound of formula 13b or the salt thereof, wherein each R¹ is independently —C(=O)(C₁-C₆)alkyl, —C(=O)(C₃-C₇)cycloalkyl or —C(=O)aryl, wherein —C(=O)aryl or —C(=O)(C₃-C₇)cycloalkyl is optionally substituted with one or more (e.g. 1, 2 or 3) (C₁-C₆)alkyl groups. In a similar manner the invention provides a method for preparing a compound of formula 13 or a salt thereof, comprising converting a compound of formula 4a or a salt thereof, to the compound of formula 13 or the salts thereof.

In one embodiment, the invention provides a method for preparing a compound of formula 13b:

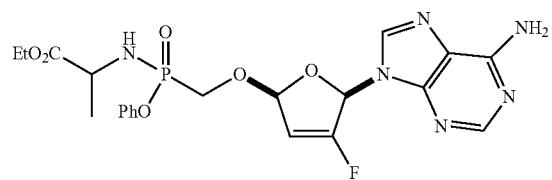

13b or a salt thereof, comprising converting a compound of formula 3a:

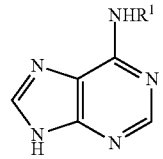

3a or a salt thereof, to the compound of formula 13b or the salt thereof, wherein R¹ is —C(=O)(C₁-C₆)alkyl, —C(=O)(C₃-C₇)cycloalkyl or —C(=O)aryl, wherein —C(=O)(C₃-C₇)cycloalkyl or —(=O)aryl is optionally substituted with one or more (e.g. 1, 2 or 3) (C₁-C₆)alkyl groups. In a similar manner the invention provides a method for preparing a compound of formula 13 or a salt thereof, comprising converting a compound of formula 3a or a salt thereof, to the compound of formula 13 or the salt thereof.

In one embodiment, the invention provides a method for preparing a compound of formula 13b:

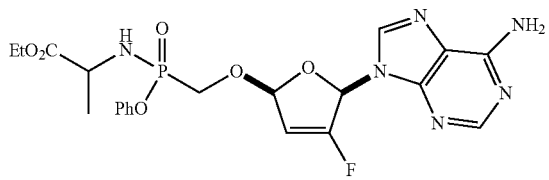

13b or a salt thereof, comprising converting a compound of formula 16:

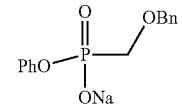

16 to the compound of formula 13b or the salt thereof. In a similar manner the invention provides a method for preparing a compound of formula 13 or a salt thereof, comprising converting a compound of formula 16 or a salt thereof, to the compound of formula 13 or the salt thereof.

In one embodiment, the invention provides a method for preparing a compound of formula 13b:

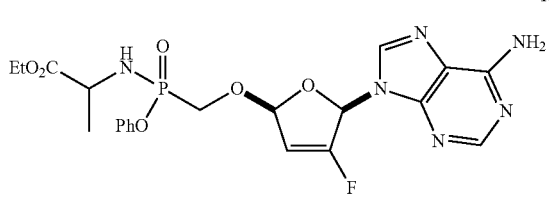

13b or a salt thereof, comprising converting a compound of formula 18b:

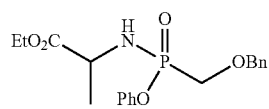

18b to the compound of formula 13b or the salt thereof. In a similar manner the invention provides a method for preparing a compound of formula 13 or a salt thereof, comprising converting a compound of formula 18 or a salt thereof, to the compound of formula 13 or the salt thereof.

In one embodiment, the invention provides a method for preparing a compound of formula 13b:

13b

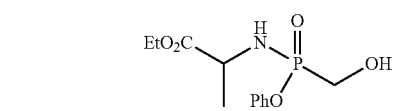

or a salt thereof, comprising converting a compound of formula 19b:

19b

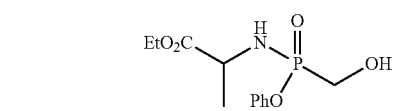

to the compound of formula 13b or the salt thereof. In a similar manner the invention provides a method for preparing a compound of formula 13 or a salt thereof, comprising converting a compound of formula 19 or a salt thereof, to the compound of formula 13 or the salt thereof.

In one embodiment the invention provides a compound selected from:

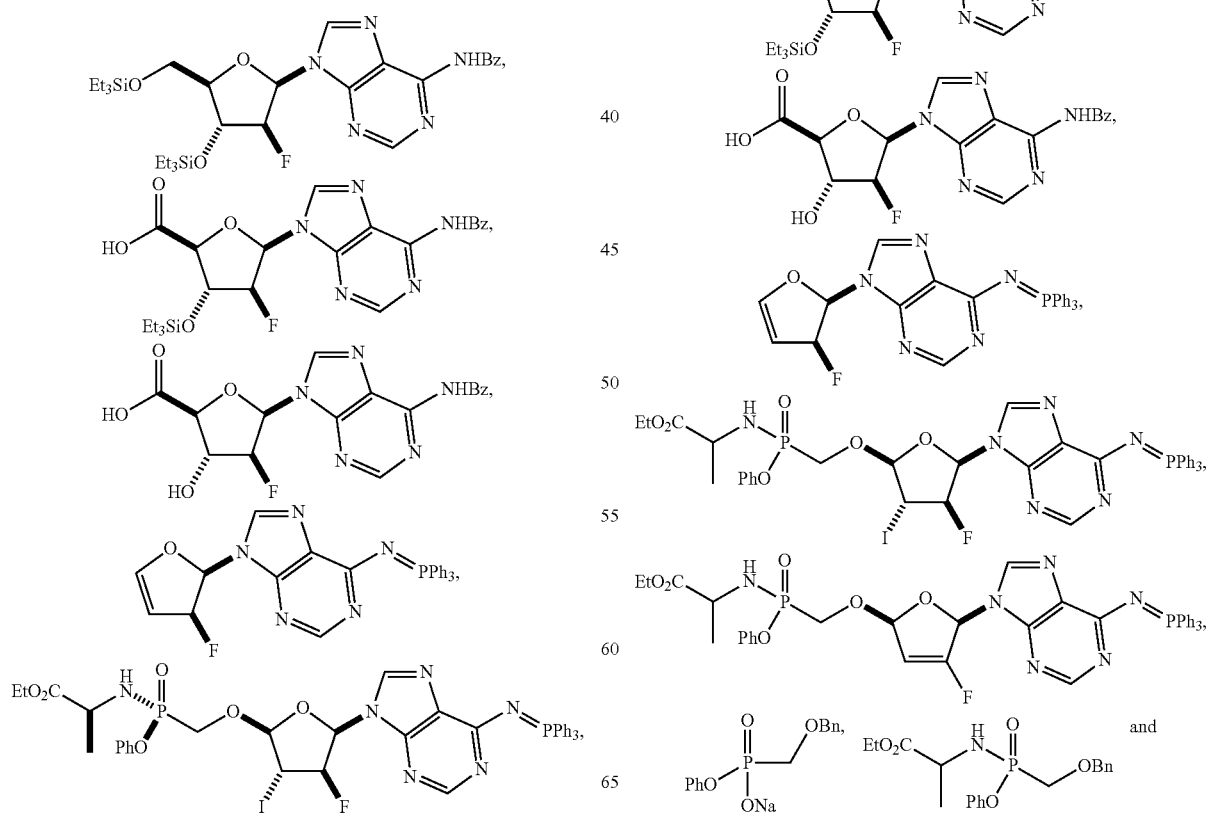

-continued

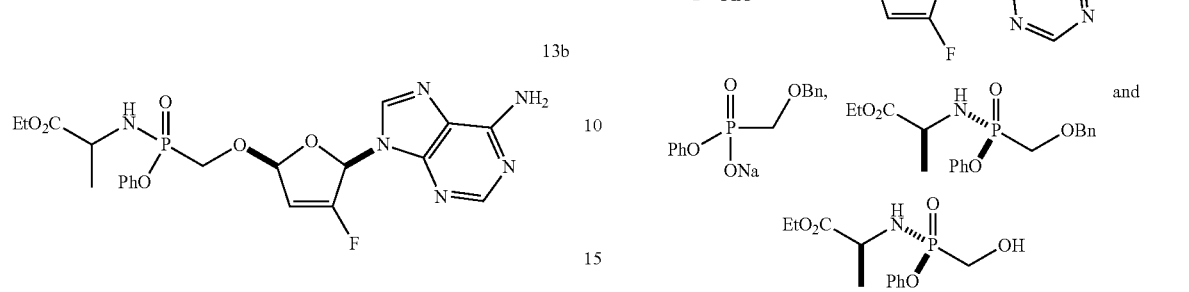

and salts thereof, which compounds are useful intermediates for preparing the compound of formula 13 and 13b or salts thereof.

In another embodiment the invention provides a compound selected from:

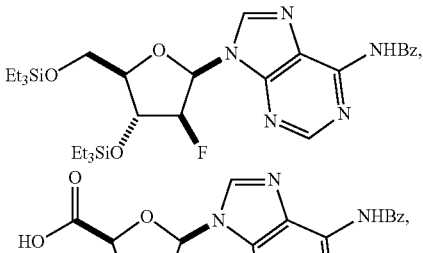

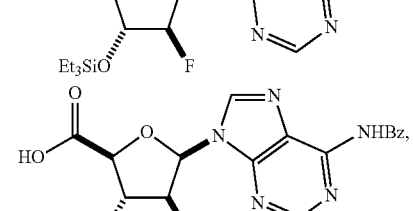

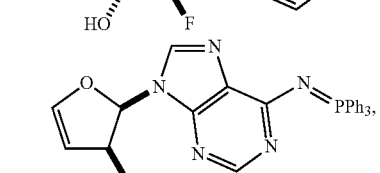

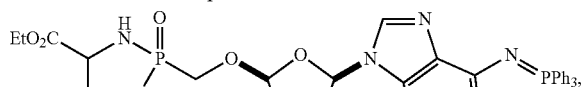

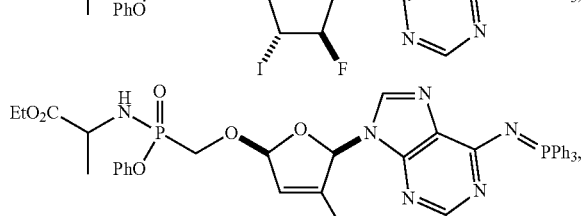

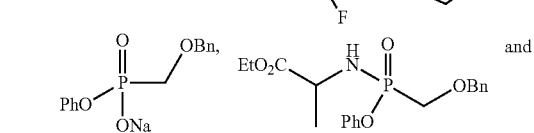

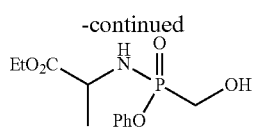

and salts thereof, which compounds are useful intermediates for preparing the compounds of formula 13 or 13b or salts or stereoisomers thereof.

In another embodiment the invention provides a compound selected from:

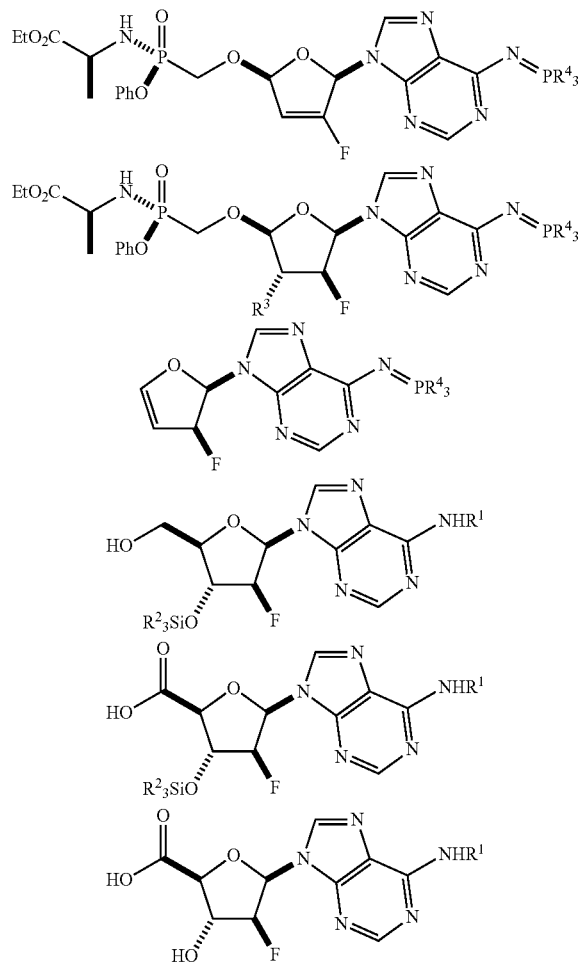

wherein:

each $R^1$ is independently —C(=O)($C_1$-$C_6$)alkyl, —C(=O)($C_3$-$C_7$)cycloalkyl or —C(=O)aryl, wherein —C(=O)($C_3$-$C_7$)cycloalkyl or —C(=O)aryl is optionally substituted with one or more (e.g. 1, 2 or 3) ($C_1$-$C_6$)alkyl groups;

each $R^2$ is independently aryl or ($C_1$-$C_6$)alkyl, wherein aryl is optionally substituted with one or more (e.g. 1, 2 or 3) ($C_1$-$C_6$)alkyl groups;

$R^3$ is I, $R^5$Se or $R^5$S;

each $R^4$ is independently ($C_1$-$C_6$)alkyl, ($C_3$-$C_7$)cycloalkyl or aryl, wherein aryl or ($C_3$-$C_7$)cycloalkyl is optionally substituted with one or more (e.g. 1, 2 or 3) ($C_1$-$C_6$)alkyl groups; and each $R^5$ is independently ($C_1$-$C_6$)alkyl, ($C_3$-$C_7$)cycloalkyl or aryl, wherein aryl or ($C_3$-$C_7$)cycloalkyl is optionally substituted with one or more (e.g. 1, 2 or 3) ($C_1$-$C_6$)alkyl groups;

and salts thereof, which compounds are useful intermediates for preparing the compound of formula 13 or 13b or salts thereof.

In another embodiment the invention provides a compound selected from:

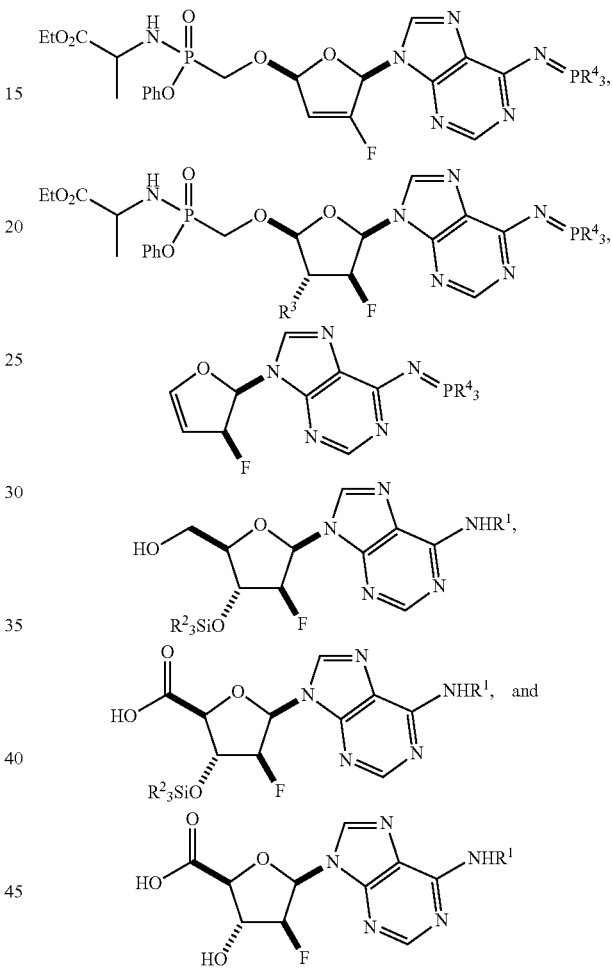

wherein;

each $R^1$ is independently —C(=O)($C_1$-$C_6$)alkyl, —C(=O)($C_3$-$C_7$)cycloalkyl or —C(=O)aryl, wherein —C(=O)($C_3$-$C_7$)cycloalkyl or —C(=O)aryl is optionally substituted with one or more (e.g. 1, 2 or 3) ($C_1$-$C_6$)alkyl groups;

each $R^2$ is independently aryl or ($C_1$-$C_6$)alkyl, wherein aryl is optionally substituted with one or more (e.g. 1, 2 or 3) ($C_1$-$C_6$)alkyl groups;

$R^3$ is I, $R^5$Se or $R^5$S;

each $R^4$ is independently ($C_1$-$C_6$)alkyl, ($C_3$-$C_7$)cycloalkyl or aryl, wherein aryl or ($C_3$-$C_7$)cycloalkyl is optionally substituted with one or more (e.g. 1, 2 or 3) ($C_1$-$C_6$)alkyl groups; and each $R^5$ is independently ($C_1$-$C_6$)alkyl, ($C_3$-$C_7$)cycloalkyl or aryl, wherein aryl or ($C_3$-$C_7$)cycloalkyl is optionally substituted with one or more (e.g. 1, 2 or 3) ($C_1$-$C_6$)alkyl groups;

and salts thereof, which compounds are useful intermediates for preparing the compounds of formula 13 or 13b or salts or stereoisomers thereof.

In another embodiment the invention provides a compound selected from:

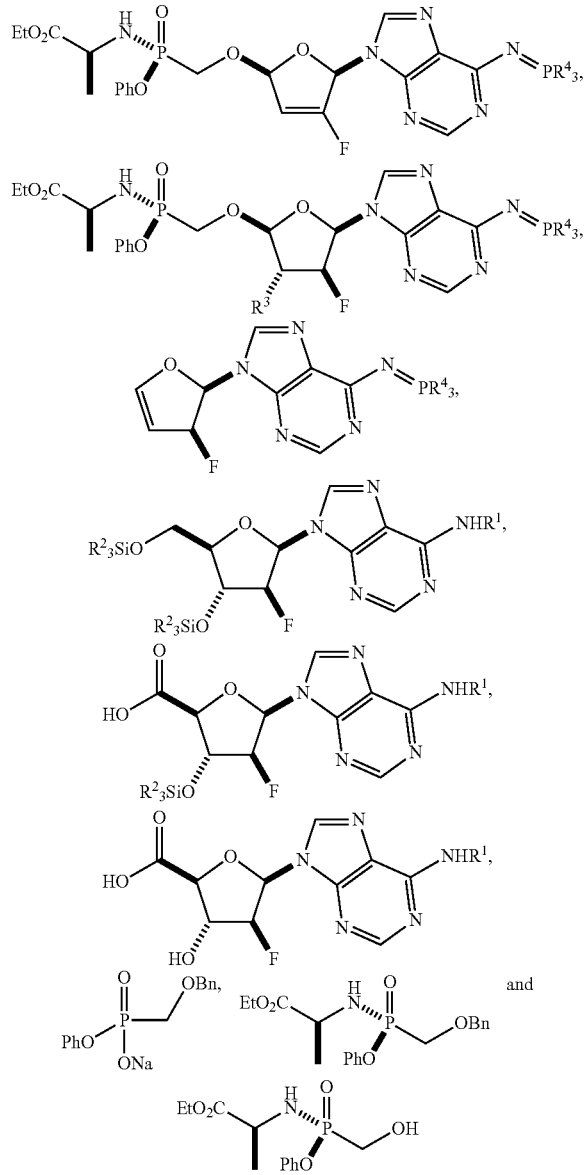

wherein;

Bn is optionally substituted with one or more (e.g. 1, 2 or 3) groups selected from (C$_1$-C$_6$)alkyl and —O(C$_1$-C$_6$)alkyl groups;

each R$^1$ is independently —C(═O)(C$_1$-C$_6$)alkyl, —C(═O)(C$_3$-C$_7$)cycloalkyl or —C(═O)aryl, wherein —C(═O)(C$_3$-C$_7$)cycloalkyl or —C(═O)aryl is optionally substituted with one or more (e.g. 1, 2, 3, 4 or 5) (C$_1$-C$_6$) alkyl groups;

each R$^2$ is independently aryl or (C$_1$-C$_6$)alkyl, wherein aryl is optionally substituted with one or more (e.g. 1, 2, 3, 4 or 5) (C$_1$-C$_6$)alkyl groups;

R$^3$ is I, R$^5$Se or R$^5$S;

each R$^4$ is independently (C$_1$-C$_6$)alkyl, (C$_3$-C$_7$)cycloalkyl or aryl, wherein aryl or (C$_3$-C$_7$)cycloalkyl is optionally substituted with one or more (e.g. 1, 2, 3, 4 or 5) (C$_1$-C$_6$) alkyl groups; and each R$^5$ is independently (C$_1$-C$_6$)alkyl, (C$_3$-C$_7$)cycloalkyl or aryl, wherein aryl or (C$_3$-C$_7$)cycloalkyl is optionally substituted with one or more (e.g. 1, 2, 3, 4 or 5) (C$_1$-C$_6$) alkyl groups;

and salts thereof, which compounds are useful intermediates for preparing the compounds of formula 13 or 13b or salts or stereoisomers thereof.

In one embodiment the invention provides a method of preparing a compound of formula 4a:

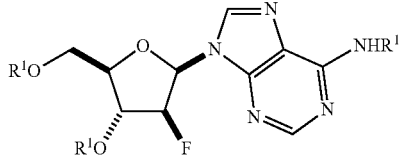

4a or a salt thereof, comprising reacting a corresponding compound of formula 2a:

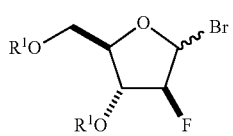

2a with a corresponding compound of formula 3a:

3a or a salt thereof, to provide the compound of formula 4a or the salt thereof, wherein each R$^1$ is independently —C(═O)(C$_1$-C$_6$)alkyl, —C(═O)(C$_3$-C$_7$)cycloalkyl or —C(═O)aryl, wherein —C(═O)(C$_3$-C$_7$)cycloalkyl or —C(═O)aryl is optionally substituted with one or more (e.g. 1, 2 or 3) (C$_1$-C$_6$)alkyl groups; and provided the compound of formula 3a is not a sodium salt of 3a when the R$^1$ group of the compound of formula 3a is benzoyl.

The compound of formula 2a can be prepared from a corresponding compound of formula 1a:

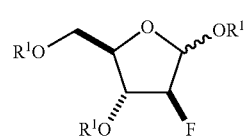

1a wherein each R$^1$ is independently —C(═O)(C$_1$-C$_6$)alkyl, —C(═O)(C$_3$-C$_7$)cycloalkyl or —C(═O)aryl, wherein —C(═O)(C$_3$-C$_7$)cycloalkyl or —C(═O)aryl is optionally substituted with one or more (e.g. 1, 2 or 3) (C$_1$-C$_6$)alkyl groups.

The compound of formula 1a can be converted to a compound of formula 4a (via the compound 2a) by treatment with a brominating agent (e.g. HBr in acetic acid, bromotrimethylsilane or titanium (IV) bromide) followed by N-glycosylation with a compound of formula 3a. The bromination and N-glycosylation can be conveniently carried out in a variety of polar and nonpolar solvents (e.g. methylene chloride, tetrahydrofuran, N-methylpyrrolidinone, acetonitrile, methyl t-butyl ether, isopropyl acetate or toluene) or combinations thereof. The bromination can be conveniently conducted at a temperature of about 0° C. The N-glycosylation can be conveniently conducted at a temperature of about 60° C. to 70° C. The document EP 0428109 describes the preparation of the compound of formula 4a from condensation of the compound of formula 2a and the sodium salt of the compound of formula 3a (each $R^1$ is benzoyl). In contrast, the N-glycosylation of the instant invention can be carried out without converting the compound of formula 3a to the sodium salt prior to or during the condensation reaction with the compound of formula 2a. Since this procedure does not use the sodium salt of the adenine derivative 3a it avoids the use of hazardous reagents such as sodium hydride. The procedure also resulted in a significantly improved anomeric ration of 24:1 versus the anomeric ratio of 15:1 reported in EP 0428109. Thus, this method represents a significant advantage over the analogous reaction described in EP 0428109.

In another embodiment the invention further provides a method for the conversion of a compound of formula 4a or a salt thereof to a compound of formula 13 or a salt thereof or a compound of formula 13b or a salt thereof, comprising converting the compound of formula 4a or the salt thereof, to the compound of formula 13 or the salt thereof or the compound of formula 13b or the salt thereof, by any of the steps outlined in Scheme 1 or Scheme 2 and described herein below.

In another embodiment the invention further provides a method for the conversion of a compound of formula 3a or a salt thereof to a compound of formula 13 or a salt thereof or a compound of formula 13b or a salt thereof, comprising converting the compound of formula 3a or the salt thereof, to the compound of formula 13 or the salt thereof or the compound of formula 13b or the salt thereof, by any of the steps outlined in Scheme 1 or Scheme 2 and described herein below.

In one embodiment the invention provides a method of preparing a compound of formula 5a:

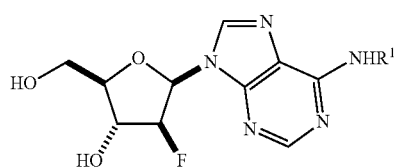

5a or a salt thereof, comprising converting a corresponding compound of formula 4a:

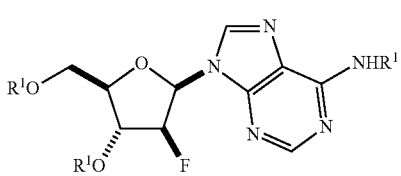

4a or a salt thereof, to the compound of formula 5a or the salt thereof, wherein each $R^1$ is independently —C(=O)($C_1$-$C_6$)alkyl, —C(=O)($C_3$-$C_7$)cycloalkyl or —C(=O)aryl, wherein —C(=O)aryl or —C(=O)($C_3$-$C_7$)cycloalkyl is optionally substituted with one or more (e.g. 1, 2 or 3) ($C_1$-$C_6$)alkyl groups.

The compound of formula 4a can be converted to a compound of formula 5a by treatment with a deprotecting agent (e.g. sodium hydroxide, triethylamine, potassium cyanide or boron trifluoride diethyl etherate). In one embodiment the deprotecting agent is a base such as a metal hydroxide (e.g. sodium hydroxide). The deprotection step can be conveniently carried out in a variety of solvents (e.g. tetrahydrofuran, organic alcohols or water) or a combination thereof. The deprotection can be conveniently conducted at a temperature of about 0° C. to 6° C. In one embodiment the deprotection step can be carried out at a temperature of about 3° C.

In another embodiment the invention further provides a method for the conversion of a compound of formula 5a or a salt thereof to a compound of formula 13 or a salt thereof or a compound of formula 13b or a salt thereof, comprising converting the compound of formula 5a or the salt thereof, to the compound of formula 13 or the salt thereof or a compound of formula 13b or the salt thereof, by any of the steps outline in Scheme 1 or Scheme 2 and described herein below.

In one embodiment the invention provides a method of preparing a compound of formula 7a:

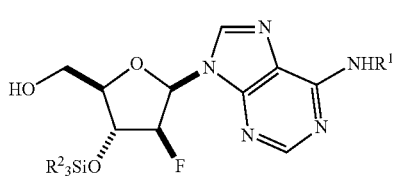

7a or a salt thereof, comprising converting a corresponding compound of formula 5a:

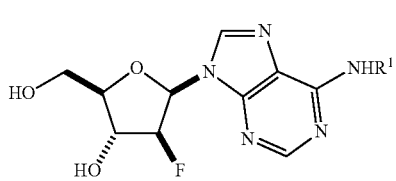

5a or a salt thereof, to the compound of formula 7a or the salt thereof, wherein $R^1$ is —C(=O)($C_1$-$C_6$)alkyl, —C(=O)($C_3$-$C_7$)cycloalkyl or —C(=O)aryl, wherein —C(=O)($C_3$-$C_7$)cycloalkyl or —C(=O)aryl is optionally substituted with one or more (e.g. 1, 2 or 3) ($C_1$-$C_6$)alkyl groups; and each $R^2$ is independently ($C_1$-$C_6$)alkyl.

In another embodiment the invention provides a method of preparing a compound of formula 7a:

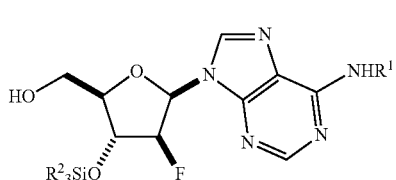

7a or a salt thereof, comprising desilylating a corresponding compound of formula 6a:

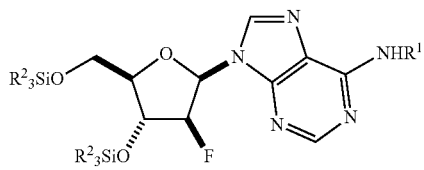

or a salt thereof, to the compound of formula 7a or the salt thereof, wherein $R^1$ is —C(=O)($C_1$-$C_6$)alkyl, —C(=O)($C_3$-$C_7$)cycloalkyl or —C(=O)aryl, wherein —C(=O)($C_3$-$C_7$)cycloalkyl or —C(=O)aryl is optionally substituted with one or more (e.g. 1, 2 or 3) ($C_1$-$C_6$)alkyl groups; and each $R^2$ is independently aryl or ($C_1$-$C_6$)alkyl, wherein aryl is optionally substituted with one or more (e.g. 1, 2 or 3) ($C_1$-$C_6$)alkyl groups.

In another embodiment the invention provides a method of preparing a compound of formula 6a:

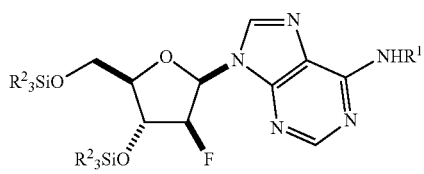

or a salt thereof, comprising silylating a corresponding compound of formula 5a:

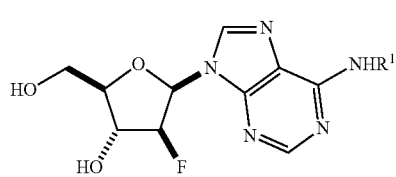

or a salt thereof, to the compound of formula 6a or the salt thereof, wherein $R^1$ is —C(=O)($C_1$-$C_6$)alkyl, —C(=O)($C_3$-$C_7$)cycloalkyl or —C(=O)aryl, wherein —C(=O)($C_3$-$C_7$)cycloalkyl or —C(=O)aryl is optionally substituted with one or more (e.g. 1, 2 or 3) ($C_1$-$C_6$)alkyl groups; and each $R^2$ is independently aryl or ($C_1$-$C_6$)alkyl, wherein aryl is optionally substituted with one or more (e.g. 1, 2 or 3) ($C_1$-$C_6$)alkyl groups.

The compound of formula 5a can be converted to the compound of formula 7a by treatment with a silylating agent in the presence of suitable base, followed by treatment with a desilylating agent. Suitable silylating agents include but are not limited to chlorotriethylsilane, bromotriethylsilane, triethyliodosilane, triethylsilane, N-triethylsilylacetamide and triethylsilyldiethylamine while suitable bases include but are not limited to diisopropylethylamine, triethylamine, N-methyl morpholine, quinuclidine, N-methylpiperidine, N-methyl pyrrolidine, potassium carbonate and sodium bicarbonate. Desilylating agents include but are not limited to p-toluenesulfonic acid monohydrate, tetrabutylammonium fluoride, various acids such as acetic acid, ion exchange resins (e.g. Dowex), hydrogen fluoride, sodium fluoride, potassium fluoride or trifluoroacetic acid. The silyation-desilylation can be conveniently carried out in a variety of solvents (e.g. toluene, methanol, acetonitrile, dimethylformamide, methylene chloride or tetrahydrofuran) or combinations thereof. The silylation can be conveniently carried out at a temperature of about 50° C. to 80° C. In one embodiment the silylation can be carried out as a temperature of about 50° C. The desilylation can be conveniently carried out at a temperature of about −20° C. to 6° C. In one embodiment the desilylation can be carried out at a temperature of about 3° C.

In another embodiment the invention further provides a method for the conversion of a compound of formula 7a or a salt thereof to a compound of formula 13 or a salt thereof or a compound of formula 13b or a salt thereof, comprising converting the compound of formula 7a or the salt thereof, to the compound of formula 13 or the salt thereof or a compound of formula 13b or the salt thereof, by any of the steps outline in Scheme 1 or Scheme 2 and described herein below.

In another embodiment the invention further provides a method for the conversion of a compound of formula 6a or a salt thereof to a compound of formula 13 or a salt thereof or a compound of formula 13b or a salt thereof, comprising converting the compound of formula 6a or the salt thereof, to the compound of formula 13 or the salt thereof or a compound of formula 13b or the salt thereof, by any of the steps outlined in Scheme 1 or Scheme 2 and described herein.

In one embodiment the invention provides a method of preparing a compound of formula 9:

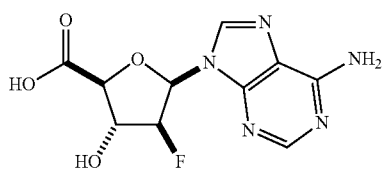

or a salt thereof, comprising converting a compound of formula 7a:

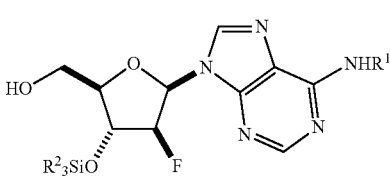

or a salt thereof, to the compound of formula 9 or the salt thereof, wherein $R^1$ is —C(=O)($C_1$-$C_6$)alkyl, —C(=O)($C_3$-$C_7$)cycloalkyl or —C(=O)aryl, wherein —(=O)($C_3$-$C_7$)cycloalkyl or —C(=O)aryl is optionally substituted with one or more (e.g. 1, 2 or 3) ($C_1$-$C_6$)alkyl groups; and each $R^2$ is independently aryl or ($C_1$-$C_6$)alkyl, wherein aryl is optionally substituted with one or more (e.g. 1, 2 or 3) ($C_1$-$C_6$)alkyl groups.

In another embodiment the invention provides a method of preparing a compound of formula 9:

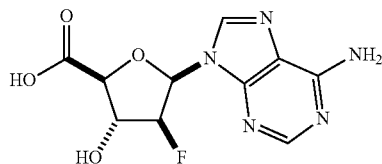

9 or a salt thereof, comprising converting a compound of formula 8a:

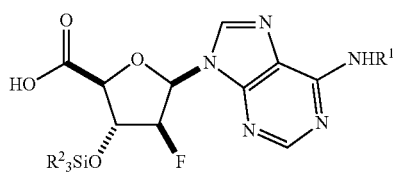

8a or a salt thereof, to the compound of formula 9 or the salt thereof, wherein $R^1$ is —C(=O)($C_1$-$C_6$)alkyl, —C(=O)($C_3$-$C_7$)cycloalkyl or —C(=O)aryl, wherein —C(=O)($C_3$-$C_7$)cycloalkyl or —C(=O)aryl is optionally substituted with one or more (e.g. 1, 2 or 3) ($C_1$-$C_6$)alkyl group; and each $R^2$ is independently aryl or ($C_1$-$C_6$)aryl, wherein aryl is optionally substituted with one or more (e.g. 1, 2 or 3) ($C_1$-$C_6$)alkyl groups.

In another embodiment the invention provides a method of preparing a compound of formula 8a:

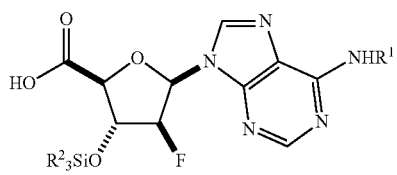

8a or a salt thereof, comprising converting a compound of formula 7a:

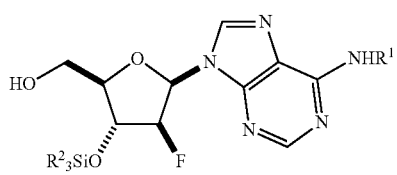

7a or a salt thereof, to the compound of formula 8a or the salt thereof, wherein $R^1$ is —C(=O)($C_1$-$C_6$)alkyl, —C(=O)($C_3$-$C_7$)cycloalkyl or —C(=O)aryl, wherein —C(=O)($C_3$-$C_7$)cycloalkyl or —C(=O)aryl is optionally substituted with one or more (e.g. 1, 2 or 3) ($C_1$-$C_6$)alkyl groups; and each $R^2$ is independently aryl or ($C_1$-$C_6$)alkyl, wherein aryl is optionally substituted with one or more (e.g. 1, 2 or 3) ($C_1$-$C_6$)alkyl groups.

In another embodiment the invention provides a method of preparing a compound of formula 9:

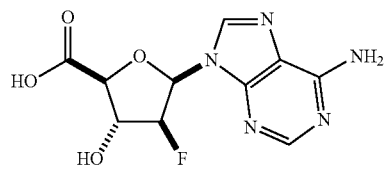

9 or a salt thereof, comprising converting a compound of formula 8'a:

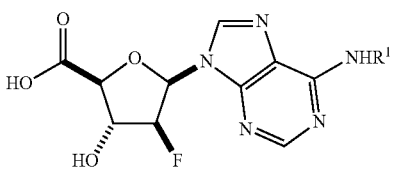

8'a or a salt thereof, to the compound of formula 9 or the salt thereof, wherein $R^1$ is —C(=O)($C_1$-$C_6$)alkyl, —C(=O)($C_3$-$C_7$)cycloalkyl or —(=O)aryl, wherein —C(=O)($C_3$-$C_7$)cycloalkyl or —C(=O)aryl is optionally substituted with one or more (e.g. 1, 2 or 3) ($C_1$-$C_6$)alkyl groups.

In another embodiment the invention provides a method of preparing a compound of formula 8'a:

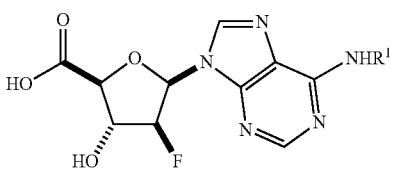

8'a or a salt thereof, comprising converting a compound of formula 7a:

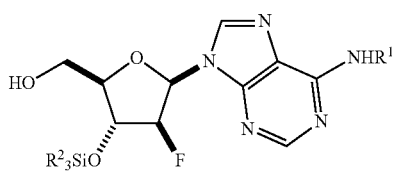

7a or a salt thereof, to the compound of formula 8'a or the salt thereof, wherein $R^1$ is —C(=O)($C_1$-$C_6$)alkyl, —C(=O)($C_3$-$C_7$)cylcoalkyl or —C(=O)aryl, wherein —C(=O)($C_3$-$C_7$)cycloalkyl or —C(=O)aryl is optionally substituted with one or more (e.g. 1, 2 or 3) ($C_1$-$C_6$)alkyl groups; and each $R^2$ is independently aryl or ($C_1$-$C_6$)alkyl, wherein aryl is optionally substituted with one or more (e.g. 1, 2 or 3) ($C_1$-$C_6$)alkyl groups.

The compound of formula 7a can be converted to the compound of formula 9 by treatment with an oxidant in the presence of suitable base followed by treatment with deacylating agent. Suitable oxidants include but are not limited to 2,2,6,6-tetramethyl-1-piperidinyloxy, free radical (TEMPO) and diacetoxyiodobenzene, hypohalite in the presence of catalysts or other metals in the presence of oxygen. Suitable deacylating agents include but are not limited to bases (e.g. metal alkoxides such as but not limited to sodium methoxide or metal hydroxides). The oxidation can be conveniently carried out in a variety of solvents including but not limited to acetonitrile and water as well as other organic solvents (e.g. organic ethers, organic esters or halogenated alkanes) and water at a temperature of about 19° C. to 45° C. In one embodiment the oxidation can be carried out at ambient temperature. The deacylation can be conveniently carried out in a variety of solvents (e.g. methanol, toluene, organic ethers, organic esters or halogenated alkanes) at a temperature of about 19° C. to 25° C. In one embodiment the deacylation can be carried out at ambient temperature.

In another embodiment the invention further provides a method for the conversion of a compound of formula 7a or a salt thereof to a compound of formula 13 or a salt thereof or a compound of formula 13b or a salt thereof, comprising converting the compound of formula 7a or the salt thereof, to the compound of formula 13 or the salt thereof or a compound of formula 13b or the salt thereof, by an of the steps outlined in Scheme 1 or Scheme 2 and described herein below.

In another embodiment the invention further provides a method for the conversion of a compound of formula 8a or a salt thereof to a compound of formula 13 or a salt thereof or a compound of formula 13b or a salt thereof, comprising converting the compound of formula 8a or the salt thereof, to the compound of formula 13 or the salt thereof or a compound of formula 13b or the salt thereof, by any of the steps outline in Scheme 1 or Scheme 2 and described herein below.

In another embodiment the invention further provides a method for the conversion of a compound of formula 8'a or a salt thereof to a compound of formula 13 or a salt thereof or a compound of formula 13b or a salt thereof, comprising converting the compound of formula 8'a or the salt thereof, to the compound of formula 13 or the salt thereof or a compound of formula 13b or the salt thereof, by any of the steps outlined in Scheme 1 or Scheme 2 and described herein below.

In one embodiment the invention provides a method of preparing a compound of formula 10a:

10a or a salt thereof, comprising converting a compound of formula 9:

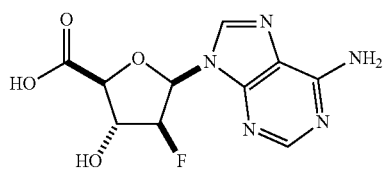

9 or a salt thereof, to the compound of formula 10a or the salt thereof, wherein each $R^4$ is independently $(C_1-C_6)$alkyl, $(C_3-C_7)$cycloalkyl or aryl, wherein aryl or $(C_3-C_7)$cycloalkyl is optionally substituted with one or more (e.g. 1, 2 or 3) $(C_1-C_6)$alkyl groups.

The compound of formula 9 can be converted to the compound of formula 10a by treatment with a decarboxylative dehydration agent including but not limited to triphenylphosphine and diisopropyl azodicarboxylate as well as other combination of aryl or alkyl phosphines and various azodicarboxylates. The decarboxylative dehydration can be conveniently carried out in a variety of solvents (e.g. tetrahydrofuran, organic ethers, organic esters or halogenated alkanes) at a temperature of about 0° C. to 50° C. In one embodiment the decarboxylative dehydration can be carried out at a temperature of about 22° C.

In another embodiment the invention further provides a method for the conversion of a compound of formula 10a or a salt thereof to a compound of formula 13 or a salt thereof or a compound of formula 13b or a salt thereof, comprising converting the compound of formula 10a or the salt thereof, to the compound of formula 13 or the salt thereof or a compound of formula 13b or the salt thereof, by any of the steps outlined in Scheme 1 or Scheme 2 and described herein below.

In one embodiment the invention provides a method of preparing a compound of formula 11b:

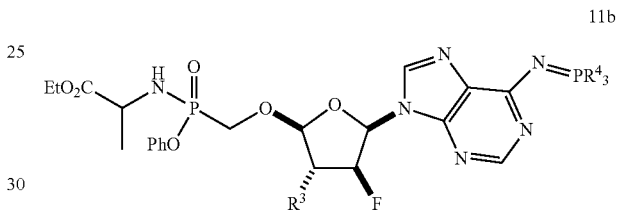

11b or a salt thereof, comprising converting a corresponding compound of formula 10a:

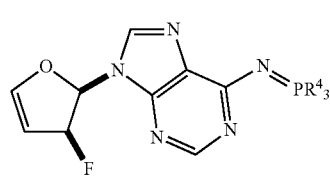

10a or a salt thereof, to the compound of formula 11b or the salt thereof, wherein, $R^3$ is I, $R^5$Se or $R^5$S and each $R^4$ and $R^5$ is independently $(C_1-C_6)$alkyl, $(C_3-C_7)$cycloalkyl or aryl, wherein aryl or $(C_3-C_7)$cycloalkyl is optionally substituted with one or more (e.g. 1, 2 or 3) $(C_1-C_6)$alkyl groups.

The compound of formula 10a can be converted to the compound of formula 11b by treatment with an etherification agent (e.g. iodine, iodine monobromide, iodine monochloride, N-iodosuccinimide, N-(phenyl-seleno) phtalimide and dimethyl(methylthio)sulfonium tetrafluoroborate) and a compound of formula 19b. The etherification can be conveniently carried out in a variety of solvents (e.g. tetrahydrofuran, organic ethers, organic esters or halogenated alkanes) at a temperature of about −50° C. to ambient temperature. In one embodiment the etherification can be carried out at a temperature of about −12° C.

In another embodiment the invention further provides a method for the conversion of a compound of formula 11a or a salt thereof or a compound of 11b or salt thereof to a compound of formula 13b or a salt thereof or a compound of formula 13a or a salt thereof respectively, comprising converting the compound of formula 11a or a salt thereof or a compound of 11b or salt thereof to a compound of formula 13b or a salt thereof or a compound of formula 13a or a salt thereof, by any of the steps outlined in Scheme 1 or Scheme 2 and described herein below.

In another embodiment the invention provides a method of preparing a compound of formula 11a:

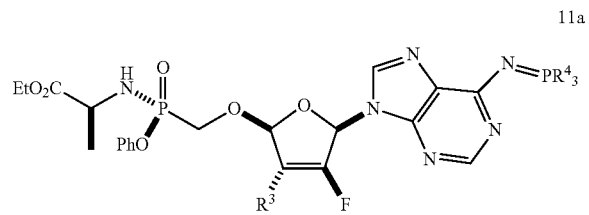

11a or a salt thereof, comprising converting a corresponding compound of formula 10a:

10a or a salt thereof, to the compound of formula 11a or the salt thereof, wherein, $R^3$ is I, $R^5Se$ or $R^5S$ and each $R^4$ and $R^5$ is independently $(C_1-C_6)$alkyl, $(C_3-C_7)$cycloalkyl or aryl, wherein aryl or $(C_3-C_7)$cycloalkyl is optionally substituted with one or more (e.g. 1, 2 or 3) $(C_1-C_6)$alkyl groups.

The compound of formula 10a can be converted to the compound of formula 11a by treatment with an etherification agent (e.g. iodine, iodine monobromide, iodine monochloride, N-iodosuccinimide, N-(phenyl-seleno) phtalimide and dimethyl(methylthio)sulfonium tetrafluoroborate) and a compound of formula 19. The etherification can be conveniently carried out in a variety of solvents (e.g. tetrahydrofuran, organic ethers, organic esters or halogenated alkanes) at a temperature of about −50° C. to ambient temperature. In one embodiment the etherification can be carried out at a temperature of about −12° C.

In one embodiment the invention provides a method of preparing a compound of formula 12b:

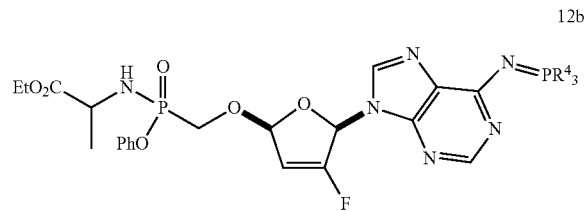

12b or a salt thereof, comprising converting a corresponding compound of formula 11b:

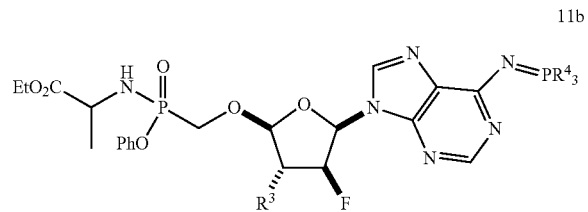

11b or a salt thereof, to the compound of formula 12b or the salt thereof, wherein $R^3$ is I, $R^5Se$ or $R^5S$ and each $R^4$ and $R^5$ is independently $(C_1-C_6)$alkyl, $(C_3-C_7)$cycloalkyl or aryl, wherein aryl or $(C_3-C_7)$cycloalkyl is optionally substituted with one or more (e.g. 1, 2 or 3) $(C_1-C_6)$alkyl groups.

In another embodiment the invention provides a method of preparing a compound of formula 12a:

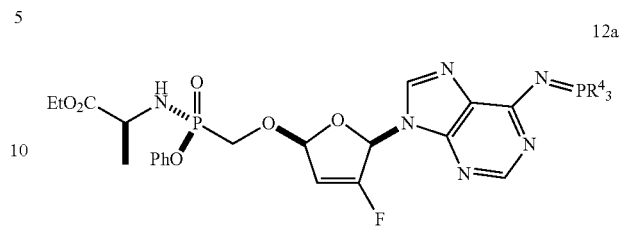

12a or a salt thereof, comprising converting a corresponding compound of formula 11a:

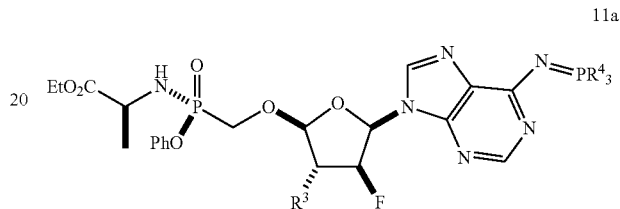

11a or a salt thereof, to the compound of formula 12a or the salt thereof, wherein $R^3$ is I, $R^5Se$ or $R^5S$ and each $R^4$ and $R^5$ is independently $(C_1-C_6)$alkyl, $(C_3-C_7)$cycloalkyl or aryl, wherein aryl or $(C_3-C_7)$cycloalkyl is optionally substituted with one or more (e.g. 1, 2 or 3) $(C_1-C_6)$alkyl groups.

The compound of formula 11b or 11a can be converted to the compound of formula 12b or 12a, respectively, by treatment with an oxidant (e.g. potassium monopersulfate, Oxone® (e.g. $2KHSO_5$—$KHSO_4$—$K_2SO_4$) or 3-chloroperbenzoic acid). The oxidation can be conveniently carried out in a variety of solvents (e.g. 2-butanone, organic ethers, organic esters or organic ketones (e.g. acetone) at a temperature of about 19° C. to 25° C. In one embodiment the oxidation can be carried out at a temperature of about 22° C.

In one embodiment the invention provides a method of preparing a compound of formula 13b:

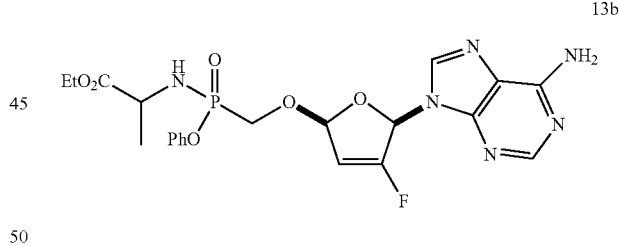

13b or salt thereof, comprising converting a compound of formula 12b:

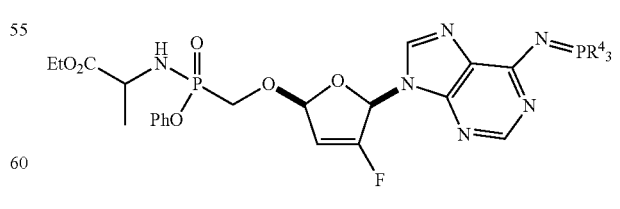

12b or a salt thereof, to the compound of formula 13b or the salt thereof, wherein each $R^4$ is independently $(C_1-C_6)$alkyl, $(C_3-C_7)$cycloalkyl or aryl, wherein any $(C_3-C_7)$cycloalkyl or aryl is optionally substituted with one or more (e.g. 1, 2 or 3) $(C_1-C_6)$alkyl groups.

In another embodiment the invention provides a method of preparing a compound of formula 13:

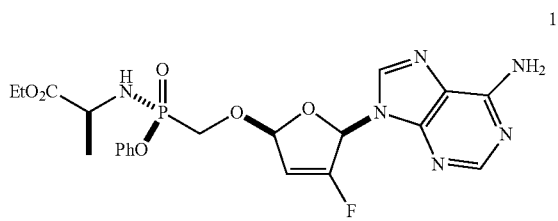

or a salt thereof, comprising converting a compound of formula 12a:

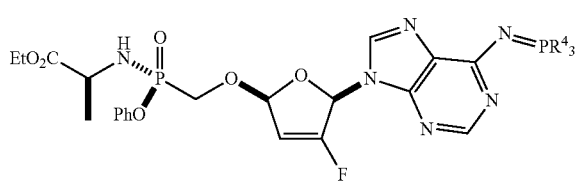

or a salt thereof, to the compound of formula 13 or the salt thereof, wherein each $R^4$ is independently $(C_1\text{-}C_6)$alkyl, $(C_3\text{-}C_7)$cycloalkyl or aryl, wherein any $(C_3\text{-}C_7)$cycloalkyl or aryl is optionally substituted with one or more (e.g. 1, 2 of 3) $(C_1\text{-}C_6)$alkyl groups.

The compound of formula 12b or 12a can be converted to the compound of formula 13b or 13, respectively, by treatment with a deprotecting agent such as an acid (e.g. acetic acid or trifluoroacetic acid). The deprotection can be conveniently carried out in a variety of solvents (e.g. water and methylene chloride, organic ethers, organic esters or organic alcohols) or combinations thereof at a temperature of about 19° C. to 25° C. In one embodiment the deprotection can be carried out at a temperature of about 22° C.

In one embodiment the invention provides a method of preparing a compound of formula 16:

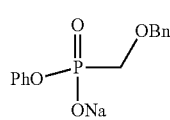

comprising converting a compound of formula 15:

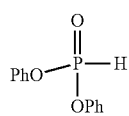

to the compound of formula 16, wherein Bn is optionally substituted with one or more (e.g. 1, 2 or 3) groups selected from $(C_1\text{-}C_6)$alkyl and —O$(C_1\text{-}C_6)$alkyl.

The compound of formula 15 can be converted to the compound of formula 16 by sequential treatment of the compound of formula 15 with (a) a silylating agent, (b) an alkylating agent, (c) a hydrolyzing agent, (d) an acid and (e) sodium chloride. The silylation can be carried out with a variety of silylating agents (e.g. bis(trimethylsilyl)trifluoroacetamide, chlorotrimethylsilane, hexamethyldisiloxane, hexamethyldisilazane, trimethylsilyldiethylamine, ethyl trimethylsiylacetate, bis(trimethylsilyl)sulfate, N,N-bistrimethylsilylurea, trimethylsilylimidazole or trimethylsilyl trifluoromethanesulfonate) in the absence of solvent (i.e. neat) at a temperature of about 30° C. to 50° C. The alkylation can be carried out with a variety of alkylating agents (e.g. benzyl chloromethyl ether or R'—CH$_2$—O—Bn wherein R'=Br, I, OTs, OTf or OMs) without solvent at a temperature of about 70° C. to 80° C. The hydrolysis can be carried out with a hydrolyzing agent such as a metal hydroxide (e.g. potassium hydroxide) in a variety of solvents (e.g. tetrahydrofuran, water, methyl t-butyl ether, dimethylformamide or toluene) and mixtures thereof. The hydrolysis can be conveniently carried out at ambient temperature. After hydrolysis and separation of the aqueous and organic layers the pH of aqueous layer can be adjusted with an acid (e.g. hydrochloric acid) and subsequently converted to the sodium salt with sodium chloride.

In another embodiment the invention further provides a method for the conversion of a compound of formula 16 to a compound of formula 13 or a salt thereof or a compound of formula 13b or a salt thereof, comprising converting the compound of formula 16, to the compound of formula 13 or the salt thereof or a compound of formula 13b or the salt thereof, by any of the steps outline in Schemes 1, 2, 3 or 4 and described herein below.

In one embodiment the invention provides a method of preparing a compound of formula 18b:

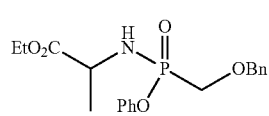

comprising converting a corresponding compound of formula 16:

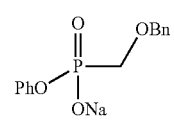

to the compound of formula 18b, wherein Bn is optionally substituted with one or more (e.g. 1, 2 or 3) groups selected from $(C_1\text{-}C_6)$alkyl and —O$(C_1\text{-}C_6)$alkyl.

The compound of formula 16 can be converted the compound of formula 18b by the sequential treatment of the compound of formula 16 with (a) a chlorinating agent and (b) alanine ethyl ester and a base. The chlorination can be carried out with a variety of chlorinating agents (e.g. oxalyl chloride, thionyl chloride and phosphorus oxychloride) in a variety of organic solvents (e.g. toluene or toluene derivatives). The chlorination can be conducted at a temperature of about −10° C. to 30° C. In one embodiment the temperature of the chlorination reaction is about 0° C. to 15° C. The reaction with alanine ethyl ester can be carried out with a variety of bases (e.g. diisopropylethylamine, trialkylamines, such as triethylamine, N-methyl morpholine or DBU, hybride bases such as sodium hydride or organolithium bases such as LiHMDS) in a suitable organic solvent (e.g. methylene chloride or a halogenated solvent) at a temperature of about 0° C. to 50° C. In one embodiment the reaction with alanine ethyl ester is carried out at ambient temperature.

In another embodiment the invention provides a method of preparing a mixture of a compound of formula 17 and a compound of formula 18:

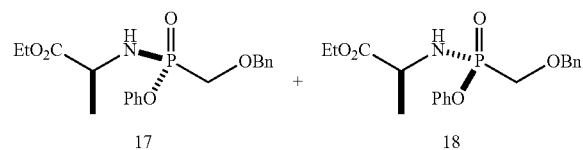

comprising converting a corresponding compound of formula 16:

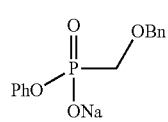

to the mixture of the compound of formula 17 and the compound of formula 18, wherein Bn is optionally substituted with one or more (e.g. 1, 2 or 3) groups selected from $(C_1-C_6)$alkyl and —$O(C_1-C_6)$alkyl.

The compound of formula 16 can be converted to a mixture of the compound of formula 17 and the compound of formula 18 by the sequential treatment of the compound of formula 16 with (a) a chlorinating agent and (b) L-alanine ethyl ester and a base. The chlorination can be carried out with a variety of chlorinating agents (e.g. oxalyl chloride, thionyl chloride and phosphorus oxychloride) in a variety of organic solvents (e.g. toluene or toluene derivatives). The chlorination can be conducted at a temperature of about −10° C. to 30° C. In one embodiment the temperature of the chlorination reaction is about 0° C. to 15° C. The reaction with L-alanine ethyl ester can be carried out with a variety of bases (e.g. diisopropylethylamine, trialkylamines, such as triethylamine, N-methyl morpholine or DBU, hybride bases such as sodium hydride or organolithium bases such as LiHMDS) in a suitable organic solvent (e.g. methylene chloride or a halogenated solvent) at a temperature of about 0° C. to 50° C. In one embodiment the reaction with L-alanine ethyl ester is carried out at ambient temperature.

In one embodiment the invention provides a method of isolating a compound of formula 18:

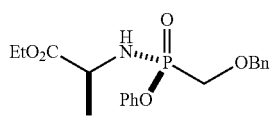

from a mixture of a corresponding compound of formula 17 and a corresponding compound of formula 18:

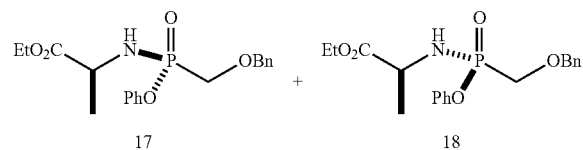

wherein Bn is optionally substituted with one or more (e.g. 1, 2 or 3) groups selected from $(C_1-C_6)$alkyl and —$O(C_1-C_6)$alkyl.

A mixture of the compound of formula 17 and the compound of formula 18 can be separated to provide the compound of formula 18. The techniques that can be used for separating a compound of formula 17 and a compound of formula 18 include but are not limited to simulated moving bed chromatography, column chromatography and stereoselective ester hydrolysis. A variety of stationary phases can be used for the chromatography methods including chiral stationary phases (e.g. Chiralpak AS®) and silica gel.

In another embodiment the invention further provides a method for the conversion of a compound of formula 17, 18 or 18b to a compound of formula 13 or a salt thereof or a compound of formula 13b or a salt thereof, comprising converting the compound of formula 17, 18 or 18b to the compound of formula 13 or the salt thereof or a compound of formula 13b or the salt thereof, by any of the steps outline in Schemes 1, 2, 3 or 4 and described herein below.

In one embodiment the invention provides a method of preparing a compound of formula 19b:

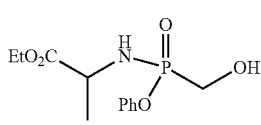

comprising converting a compound of formula 18b:

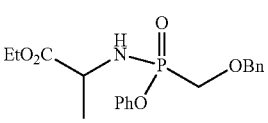

to the compound of formula 19b, wherein Bn is optionally substituted with one or more (e.g. 1, 2 or 3) groups selected from $(C_1-C_6)$alkyl and —$O(C_1-C_6)$alkyl.

In another embodiment the invention provides a method of preparing a compound of formula 19:

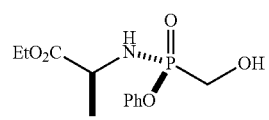

comprising converting a compound of formula 18:

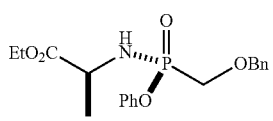

to the compound of formula 19, wherein Bn is optionally substituted with one or more (e.g. 1, 2 or 3) groups selected from $(C_1-C_6)$alkyl and —$O(C_1-C_6)$alkyl.

The compound of formula 18b or 18 can be converted to the compound of formula 19b or 19, respectively, by debenzylation including but not limited to catalytic hydrogenation such as hydrogenation in the presence of a catalyst (e.g. palladium on carbon), transfer hydrogenation using cyclohexane, cyclohexadiene, formic acid, or ammonium formate or treatment with raney nickel trimethylsilyliodosilane, $FeCl_3$, ozone or $BF_3Et_2$). The debenzylation reaction can be conducted in a variety of organic solvents (e.g. methylene chloride, acetonitrile, methyl t-butyl ether or isopropyl acetate) or mixtures thereof. The debenzylation step can be conducted at a temperature of about 0° C. to 30° C. In one embodiment the debenzylation temperature is about 22° C.

The compound of formula 17 and the debenzylated compound of formula 17, the compound of formula 17':

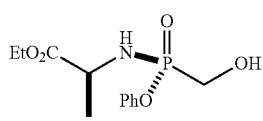

17' are also part of the invention. These compounds are useful as they can be used to prepare other compounds described in WO 2006/110157 and WO 2006/015261 which compounds are reported to be useful as anti-HIV agents.

In another embodiment the invention further provides a method for the conversion of a compound of formula 17', 19 or 19b to a compound of formula 13 or a salt thereof or a compound of formula 13b or a salt thereof, comprising converting the compound of formula 17', 19 or 19b to the compound of formula 13 or the salt thereof or a compound formula 13b or the salt thereof, by any of the steps outline in Schemes 1, 2, 3 or 4 and described herein below.

The processes and intermediates described herein can also be useful for preparing a compound of formula 21. International Patent Application Publication Number WO 2002008241 and U.S. Pat. No. 7,390,791 discuss compound 21 and report that it is useful as an anti-HIV agent.

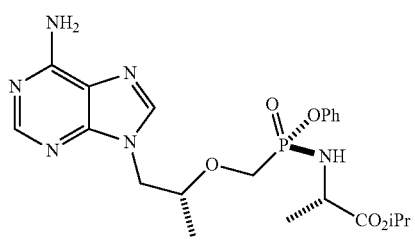

21

The methods and intermediates described herein below, which are useful for preparing the compound of formula 21 or formula 21c or the compounds of formula 21b, represent an improvement over previous methods. For example, previously reported methods required the isolation of the compound of formula 21 from a mixture of diastereomers by chiral chromatography. This method of resolution is costly as specialized equipment and significant amounts of production time and labor are needed to effectively remove the undesired compound (e.g. about 50%) from the product mixture. Additionally, the use of this method of resolution of diastereomers in the final stage of synthetic process is inherently inefficient and undesirable because the overall process transformation yield (i.e. maximum 50%) is severely impacted. The present synthesis does not require such an isolation step as the synthesis described herein utilizes a selected, stereo-defined chiral phosphonamidate (e.g. compound 25) that provides compound 21 as a single diastereomer. Accordingly, the present invention provides improved methods and intermediates for preparing compound 21 as well as compound 21c and the compounds of formula 21b.

Accordingly, in one embodiment the invention provides a method of preparing a compound of formula 21b:

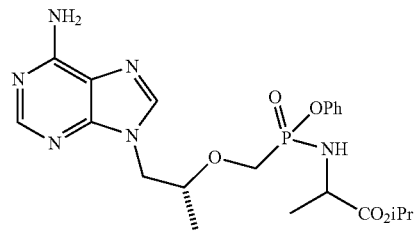

21b comprising reacting a compound of formula 20:

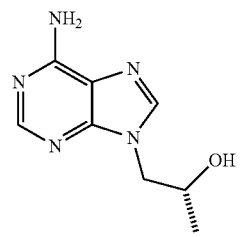

20 or a salt thereof, with a compound of formula 25b

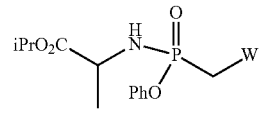

25b to provide the compound of formula 21b, wherein W is a leaving group.

In another embodiment the invention provides a method of preparing a compound of formula 21:

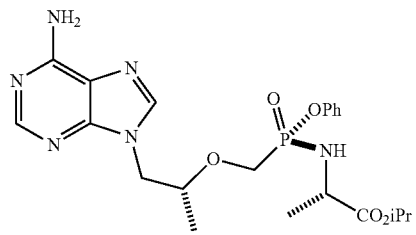

21 comprising reacting a compound of formula 20:

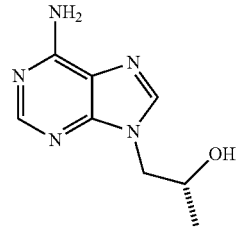

20 or a salt thereof, with a compound of formula 25:

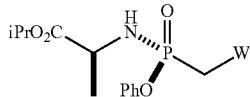

to provide the compound of formula 21, wherein W is a leaving group.

The compound of formula 20 can be converted to the compound of formula 21b or 21, respectively, by reaction with the compound of formula 25b or 25, respectively. In one embodiment the reaction involves treating the compound of formula 20 with a base. The treatment of 20 with a base can occur prior to, simultaneously, or after contact with the compound of formula 25b or 25. Bases include but are not limited to metal hydroxides (e.g. Li, Na, K, Ca or Mg hydroxides), metal alkoxides such as but not limited to a metal tert-butoxide (e.g. LiOtBu, KOtBu) or amine bases such as but not limited to triethylamine, diisopropylethylamine and pyridine. The reaction can be conducted in a variety of organic solvents (e.g. methylene chloride or ethereal solvents such as tetrahydrofuran or diethyl ether) or mixtures thereof.

In one embodiment the invention provides a method of preparing a compound of formula 23b:

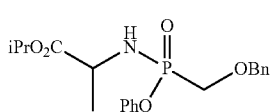

comprising converting a corresponding compound of formula 16:

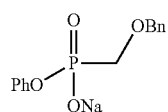

to the compound of formula 23b, wherein Bn is optionally substituted with one or more (e.g. 1, 2 or 3) groups selected from $(C_1-C_6)$alkyl or $—O(C_1-C_6)$alkyl.

The compound of formula 16 can be converted the compound of formula 23b by the same method outlined for the conversion of 16 to 18b except that alanine isopropyl ester was used instead of alanine ethyl ester.

In another embodiment the invention provides a method of preparing a mixture of a compound of formula 22 and a compound of formula 23:

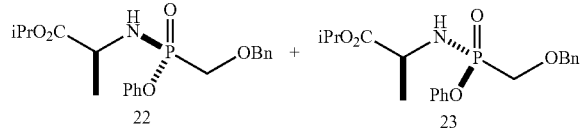

comprising converting a corresponding compound of formula 16:

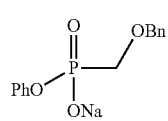

to the mixture of the compound of formula 22 and the compound of formula 23, wherein Bn is optionally substituted with one or more (e.g. 1, 2 or 3) groups selected from $(C_1-C_6)$alkyl and $—O(C_1-C_6)$alkyl.

The compound of formula 16 can be converted to a mixture of the compound of formula 22 and the compound of formula 23 by the same method used to convert the compound of formula 16 to the mixture of the compound of formula 17 and the compound of formula 18 except that L-alanine isopropyl ester was used instead of L-alanine ethyl ester.

In one embodiment the invention provides a method of isolating a compound of formula 23:

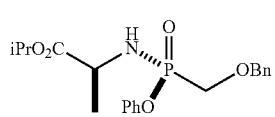

from a mixture of a compound of formula 22 and a compound of formula 23:

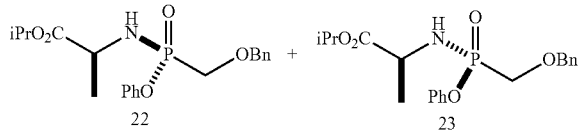

wherein Bn is optionally substituted with one or more (e.g. 1, 2 or 3) groups selected from $(C_1-C_6)$alkyl and $—O(C_1-C_6)$alkyl.

A mixture of the compound of formula 22 and the compound of formula 23 can be separated to provide the compound of formula 23 by the same method used to separate the mixture of the compound of formula 17 and the compound of formula 18 to provide the compound of formula 18.

In one embodiment the invention provides a method of preparing a compound of formula 24b:

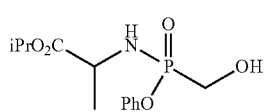

comprising converting a compound of formula 23b:

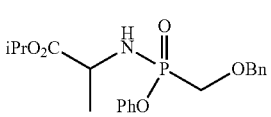

to the compound of formula 24b, wherein Bn is optionally substituted with one or more (e.g. 1, 2 or 3) groups selected from $(C_1-C_6)$alkyl and $—O(C_1-C_6)$alkyl.

In another embodiment the invention provides a method of preparing a compound of formula 24:

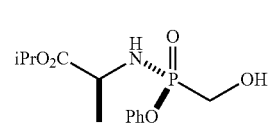

comprising converting a compound of formula 23:

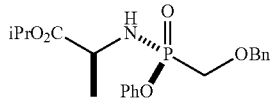

23 to the compound of formula 24, wherein Bn is optionally substituted with one or more (e.g. 1, 2 or 3) groups selected from (C$_1$-C$_6$)alkyl and —O(C$_1$-C$_6$)alkyl.

The compound of formula 23b or 23 can be converted to the compound of formula 24b or 24, respectively, by the same method used to convert the compound of formula 18b or 18 to the compound of formula 19 or 19b, respectively.

In one embodiment the invention provides a method of preparing a compound of formula 25b:

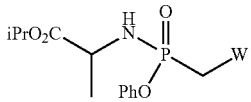

25b comprising converting a compound of formula 24b:

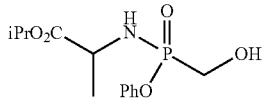

24b to the compound of formula 25b, wherein W is a leaving group.

In another embodiment the invention provides a method of preparing a compound of formula 25:

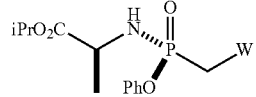

25 comprising converting a compound of formula 24:

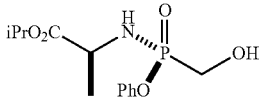

24 to the compound of formula 25, wherein W is a leaving group.

The compound of formula 24b or 24 can be converted to the compound of formula 25b or 25, respectively, by conversion of the hydroxy group to a leaving group. In one embodiment the leaving group ("W") is halo or —OS(O)$_2$R$^L$, wherein R$^L$ is (C$_1$-C$_6$)alkyl or aryl, wherein (C$_1$-C$_6$)alkyl is optionally substituted with one or more halogen, and wherein aryl is optionally substituted with one or more halogen, (C$_1$-C$_6$)alkyl or NO$_2$. When the leaving the group is a halo the conversion comprises treatment of 24 or 24b with a halogenation agent (e.g. CCl$_4$, CBr$_4$ or I$_2$ with triphenylphosphine). When the leaving the group is a sulfonate ester (e.g. —OS(O)$_2$R$^L$) the conversion comprises treatment of 24 or 24b with a sulfonating agent such as but not limited to a sulfonyl chloride or a sulfonic anhydride (e.g. methansulfonyl chloride, methanesulfonic anhydride, p-toluenesulfonyl chloride, trifluoromethanesulfonic anhydride etc.) and a base such as but limited to an amine base (triethylamine, diisopropylamine, pyridine, etc). These reactions can be carried out in a wide variety of organic solvents (e.g. methylene chloride or ethereal solvents such as tetrahydrofuran or diethyl ether) or mixtures thereof.

In one embodiment the invention provides a compound selected from:

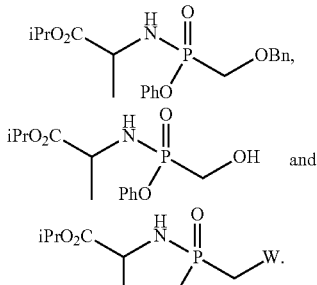

wherein Bn is optionally substituted with one or more (e.g. 1, 2 or 3) groups selected from (C$_1$-C$_6$)alkyl and —O(C$_1$-C$_6$)alkyl and W is a leaving group, which compounds are useful intermediates for preparing the compounds of formula 21b.

In another embodiment the invention provides a compound selected from:

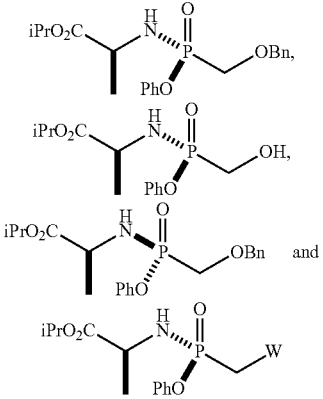

wherein Bn is optionally substituted with one or more (e.g. 1, 2 or 3) groups selected from (C$_1$-C$_6$)alkyl and —O(C$_1$-C$_6$)alkyl and W is a leaving group, which compounds are useful intermediates for preparing the compounds of formula 21.

International Patent Application Publication Number WO2002008241 and U.S. Pat. No. 7,390,791 discuss compound 21c and report that it is useful as an anti-HIV agent.

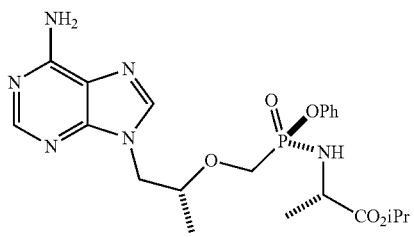

21c

Accordingly, in one embodiment the invention provides a method of preparing a compound of formula 21c:

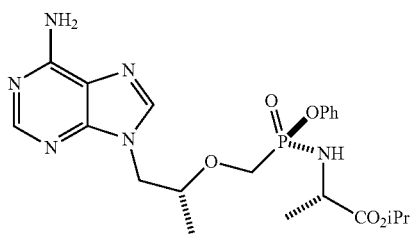

21c comprising reacting a compound of formula 20:

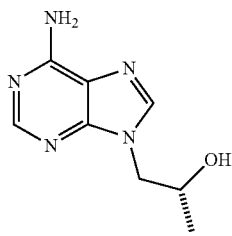

20 or a salt thereof, with a compound of formula 25c:

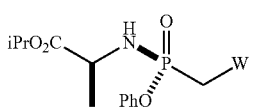

25c to provide the compound of formula 21c, wherein W is a leaving group.

The compound of formula 20 can be converted tot the compound of formula 21c by reaction with the compound of formula 25c. In one embodiment the reaction involves treating the compound of formula 20 with a base. The treatment of 20 with a base can occur prior to, simultaneously, or after contact with the compound of formula 25c. Bases include but are not limited to metal hydroxides (e.g. Li, Na, K, Ca or Mg hydroxides), metal alkoxides such as but not limited to a metal tert-butoxide (e.g. LiOtBu, KOtBu) or amines bases such as but not limited to triethylamine, diisopropylethylamine and pyridine. The reaction can be conducted in a variety of organic solvents (e.g. methylene chloride or ethereal solvents such as tetrahydrofuran or diethyl ether) or mixtures thereof.

In one embodiment the invention provides a method of isolating a compound of formula 22:

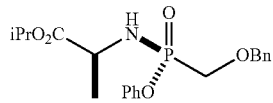

22 from a mixture of a compound of formula 22 and a compound of formula 23:

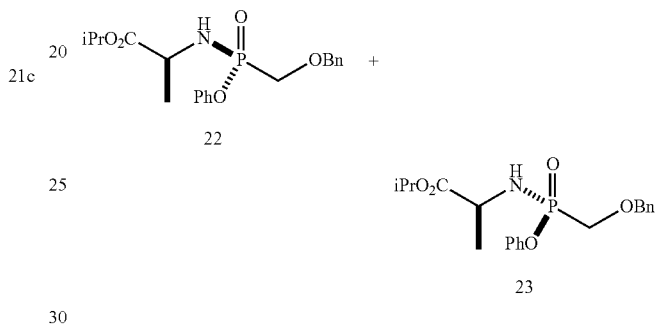

wherein Bn is optionally substituted with one or more (e.g. 1, 2 or 3) groups selected from $(C_1-C_6)$alkyl and $—O(C_1-C_6)$alkyl.

A mixture of the compound of formula 22 and the compound of formula 23 can be separated to provide the compound of formula 22 by the same method used to separate the mixture of the compound of formula 17 and the compound of formula 18 to provide the compound of formula 18.

In another embodiment the invention provides a method of preparing a compound of formula 24c:

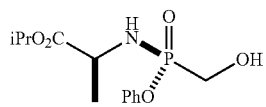

24c comprising converting a compound of formula 22:

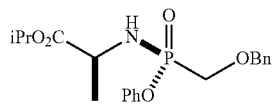

22 to the compound of formula 24c, wherein Bn is optionally substituted with one or more (e.g. 1, 2 or 3) groups selected from $(C_1-C_6)$alkyl and $—O(C_1-C_6)$alkyl.

The compound of formula 22 can be converted to the compound of formula 24c by the same method used to convert the compound of formula 18b or 18 to the compound of formula 19b or 19, respectively.

In another embodiment the invention provides a method of preparing a compound of formula 25c:

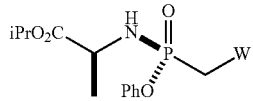

25c comprising converting a compound of formula 24c:

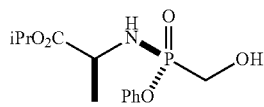

24c to the compound of formula 25c, wherein W is a leaving group.

The compound of formula 24c can be converted to the compound of formula 25c by conversion of the hydroxy group to a leaving group. In one embodiment the leaving group ("W") is halo or —OS(O)$_2$R$^L$, wherein R$^L$ is (C$_1$-C$_6$) alkyl or aryl, wherein (C$_1$-C$_6$)alkyl is optionally substituted with one or more halogen, and wherein aryl is optionally substituted with one or more halogen, (C$_1$-C$_6$)alkyl or NO$_2$. When the leaving the groups is a halo the conversion comprises treatment of 24c with a halogenating agent (e.g. CCl$_4$, CBr$_4$ or I$_2$ with triphenylphosphine). When the leaving the group is a sulfonate ester (e.g. —OS(O)$_2$R$^L$) the conversion comprises treatment of 24c with a sulfonating agent such as but not limited to a sulfonly chloride or a sulfonic anhydride (e.g. methansulfonyl chloride, methanesulfonic anhydride, p-toluenesulfonyl chloride, trifluoromethanesulfonic anhydride etc.) and a base such as but limited to an amine base (triethylamine, diisopropylamine, pyridine, etc.). These reaction can be carried out in a wide variety of organic solvents (e.g. methylene chloride or ethereal solvents such as tetrahydrofuran or diethyl ether) or mixtures thereof.

The processes described herein are useful for preparing additional phosphonamidates; these additional phosphonamidates are useful for preparing compounds that are reported to be anti-HIV agents. International Patent Application Publication Number WO 2006/110157 and International Patent Application Publication Number WO 2006/015261 describe such agents. Accordingly, the invention includes the novel phosphonamidates and processes illustrated in Schemes 9 and Scheme 10.

Accordingly, in one embodiment the invention provides a method of preparing a compound of formula 26:

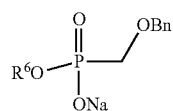

26 comprising converting a corresponding compound of formula 25:

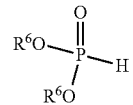

25 to the compound of formula 26, wherein Bn is optionally substituted with one or more (e.g. 1, 2 or 3) groups selected from (C$_1$-C$_6$)alkyl and —O(C$_1$-C$_6$)alkyl and R$^6$ is aryl optionally substituted with one or more groups (e.g. 1, 2, 3, 4 or 5) selected from (C$_1$-C$_6$)alkyl and —O(C$_1$-C$_6$)alkyl.

The compound of formula 25 can be converted to the compound of formula 26, by the method used to convert the compound of formula 15 to the compound of formula 16.

In one embodiment the invention provides a method of preparing a compound of formula 28b:

28b or a salt thereof, comprising converting a corresponding compound of formula 26:

26 to the compound of formula 28b or the salt thereof, wherein Bn is optionally substituted with one or more (e.g. 1, 2 or 3) groups selected from (C$_1$-C$_6$)alkyl and —O(C$_1$-C$_6$)alkyl; R$^6$ is aryl optionally substituted with one or more groups (e.g. 1, 2, 3, 4 or 5) selected from (C$_1$-C$_6$)alkyl and —O(C$_1$-C$_6$) alkyl; R$^7$ is (C$_1$-C$_6$)alkyl, (C$_3$-C$_7$)cycloalkyl, (C$_3$-C$_7$)cycloalkyl(C$_1$-C$_6$)alkyl-, aryl(C$_1$-C$_6$)alkyl- or aryl; and R$^8$ is an amino acid sidechain.

The compound of formula 26 can be converted to the compound of formula 28b by the same method outlined for the conversion of 16 or 18b except that an amino acid can be used instead of alanine ethyl ester.

In another embodiment the invention provides a method of preparing a mixture of a compound of formula 27 and a compound of formula 28:

comprising converting a corresponding compound of formula 16:

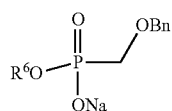

to the mixture of the compound of formula 27 and the compound of formula 28, wherein Bn is optionally substituted with one or more (e.g. 1, 2 or 3) groups selected from $(C_1-C_6)$alkyl and $-O(C_1-C_6)$alkyl; $R^6$ is aryl optionally substituted with one or more groups (e.g. 1, 2, 3, 4 or 5) selected from $(C_1-C_6)$alkyl and $-O(C_1-C_6)$alkyl; $R^7$ is $(C_1-C_{10})$alkyl, $(C_3-C_7)$cycloalkyl, $(C_3-C_7)$cycloalkyl$(C_1-C_6)$alkyl-, aryl$(C_1-C_6)$alkyl- or aryl; and $R^8$ is an amino acid sidechain.

The compound of formula 26 can be converted to a mixture of the compound of formula 27 and the compound of formula 28 by the same method used to convert a compound of formula 16 to a mixture of the compound of formula 17 and the compound of formula 18 except that an (S)-amino acid can be used instead of L-alanine ethyl ester.

In one embodiment the invention provides a method of isolating a compound of formula 28:

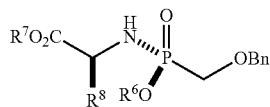

or a salt thereof from a mixture of a compound of formula 27 and a compound of formula 28:

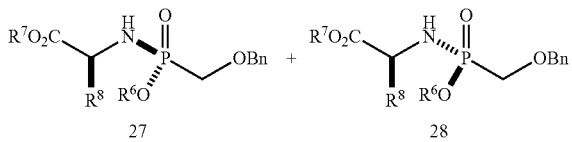

or a salts thereof, wherein Bn is optionally substituted with one or more (e.g. 1, 2 or 3) groups selected from $(C_1-C_6)$alkyl and $-O(C_1-C_6)$alkyl; $R^6$ is aryl optionally substituted with one or more groups (e.g. 1, 2, 3, 4 or 5) selected from $(C_1-C_6)$alkyl and $-O(C_1-C_6)$alkyl; $R^7$ is $(C_1-C_{10})$alkyl, $(C_3-C_7)$cycloalkyl, $(C_3-C_7)$cycloalkyl$(C_1-C_6)$alkyl-, aryl$(C_1-C_6)$alkyl- or aryl; and $R^8$ is an amino acid sidechain.

A mixture of the compound of formula 27 and the compound of formula 28 can be separated to provide the compound of formula 28 by the same method used to separate the mixture of the compound of formula 17 and the compound of formula 18 to provide the compound of formula 18.

In one embodiment the invention provides a method of preparing a compound of formula 30b:

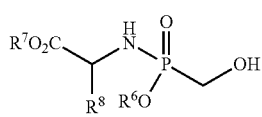

or a salt thereof, comprising converting a corresponding compound of formula 28b:

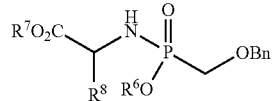

or a salt thereof to the compound of formula 30b or the salt thereof, wherein Bn is optionally substituted with one or more (e.g. 1, 2 or 3) groups selected from $(C_1-C_6)$alkyl and $-O(C_1-C_6)$alkyl; $R^6$ is aryl optionally substituted with one or more groups (e.g. 1, 2, 3, 4 or 5) selected from $(C_1-C_6)$alkyl and $-O(C_1-C_6)$alkyl; $R^7$ is $(C_1-C_{10})$alkyl, $(C_3-C_7)$cycloalkyl, $(C_3-C_7)$cycloalkyl$(C_1-C_6)$alkyl-, aryl$(C_1-C_6)$alkyl- or aryl; and $R^8$ is an amino acid sidechain.

The compound of formula 28b can be converted to the compound of formula 30b by the same method outlined for the conversion of 18b to 19b.

In another embodiment the invention provides a method of preparing a compound of formula 30:

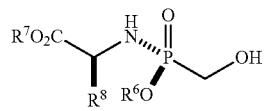

or a salt thereof, comprising converting a corresponding compound of formula 28:

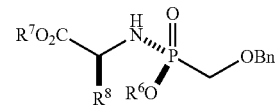

or a salt thereof to the compound of formula 30 or the salt thereof, wherein Bn is optionally substituted with one or more (e.g. 1, 2 or 3) groups selected from $(C_1-C_6)$alkyl and $-O(C_1-C_6)$alkyl; $R^6$ is aryl optionally substituted with one or more groups (e.g. 1, 2, 3, 4 or 5) selected from $(C_1-C_6)$alkyl and $-O(C_1-C_6)$alkyl; $R^7$ is $(C_1-C_{10})$alkyl, $(C_3-C_7)$cycloalkyl, $(C_3-C_7)$cycloalkyl$(C_1-C_6)$alkyl-, aryl$(C_1-C_6)$alkyl- or aryl; and $R^8$ is an amino acid sidechain.

The compound of formula 28b or 28 can be converted to the compound of formula 30b or 30, respectively, by the same method used to convert the compound of formula 18b or 18 to the compound of formula 19b or 19, respectively.

In one embodiment the invention provides a method of preparing a compound of formula 31b:

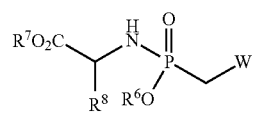

or a salt thereof, comprising converting a corresponding compound of formula 30b:

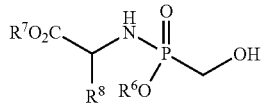

or a salt thereof to the compound of formula 31b or the salt thereof, wherein $R^6$ is aryl optionally substituted with one or more groups (e.g. 1, 2, 3, 4 or 5) selected from $(C_1-C_6)$alkyl and —$O(C_1-C_6)$alkyl; $R^7$ is $(C_1-C_{10})$alkyl, $(C_3-C_7)$cycloalkyl, $(C_3-C_7)$cycloalkyl$(C_1-C_6)$alkyl-, aryl$(C_1-C_6)$alkyl- or aryl; $R^8$ is an amino acid sidechain; and W is a leaving group.

In another embodiment the invention provides a method of preparing a compound of formula 31:

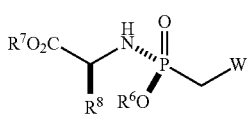

or a salt thereof, comprising converting a corresponding compound of formula 30:

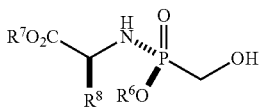

or a salt thereof to the compound of formula 31 or the salt thereof, wherein $R^6$ is aryl optionally substituted with one or more groups (e.g. 1, 2, 3, 4 or 5) selected from $(C_1-C_6)$alkyl and —$O(C_1-C_6)$alkyl; $R^7$ is $(C_1-C_{10})$alkyl, $(C_3-C_7)$cycloalkyl, $(C_3-C_7)$cycloalkyl$(C_1-C_6)$alkyl-, aryl$(C_1-C_6)$alkyl- or aryl; $R^8$ is an amino acid sidechain; and W is a leaving group.

The compound of formula 30b or 30 can be converted to the compound of formula 31b or 31, respectively, by the same method used to convert the compound of formula 24b or 24 to the compound of formula 25b or 25, respectively.

In one embodiment the invention provides a compound selected from:

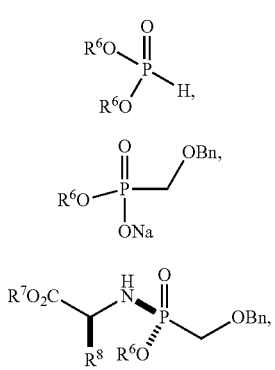

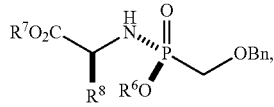

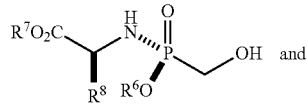

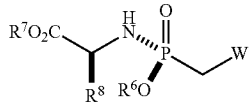

or a salt thereof, wherein Bn is optionally substituted with one or more (e.g. 1, 2 or 3) groups selected from $(C_1-C_6)$ alkyl and —$O(C_1-C_6)$alkyl; $R^6$ is aryl optionally substituted with one or more groups (e.g. 1, 2, 3, 4 or 5) selected from $(C_1-C_6)$alkyl and —$O(C_1-C_6)$alkyl; $R^7$ is $(C_1-C_{10})$alkyl, $(C_3-C_7)$cycloalkyl, $(C_3-C_7)$cycloalkyl$(C_1-C_6)$alkyl-, aryl $(C_1-C_6)$alkyl- or aryl; $R^8$ is an amino acid sidechain; and W is a leaving group, which compounds are useful intermediates for preparing certain compounds of International Patent Application Publication Number WO 2006/110157 and International Patent Application Publication Number WO 2006/015261, or salts or stereoisomers thereof.

In another embodiment the invention provides a compound selected from:

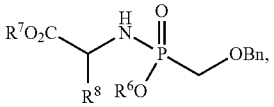

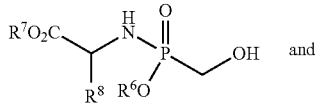

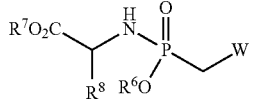

or a salt thereof, wherein Bn is optionally substituted with one or more (e.g. 1, 2 or 3) groups selected from $(C_1-C_6)$ alkyl and —$O(C_1-C_6)$alkyl; $R^6$ is aryl optionally substituted with one or more groups (e.g. 1, 2, 3, 4 or 5) selected from $(C_1-C_6)$alkyl and —$O(C_1-C_6)$alkyl; $R^7$ is $(C_1-C_{10})$alkyl, $(C_3-C_7)$cycloalkyl, $(C_3-C_7)$cycloalkyl$(C_1-C_6)$alkyl-, aryl $(C_1-C_6)$alkyl- or aryl; $R^8$ is an amino acid sidechain; and W is a leaving group, which compounds are useful intermediates for preparing certain compounds of International Patent Application Publication Number WO 2006/110157 and International Patent Application Publication Number WO 2006/015261, or salts or stereoisomers thereof.

The following provisos relate to both method and compound embodiments of the in vend on as described above.

In one embodiment the compound of formula 25 is not:

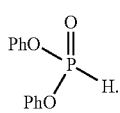

In one embodiment the compound of formula 26 is not:

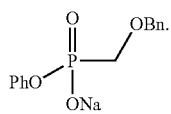

In one embodiment the compound of formula 27 or 28 is not:

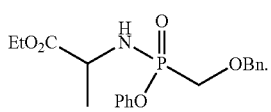

In one embodiment the compound of formula 27 or 28 is not:

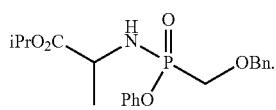

In one embodiment the compound of formula 28b is not:

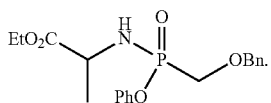

In one embodiment the compound of formula 28b is not:

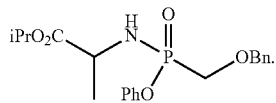

In one embodiment the compound of formula 30 or 30b is not:

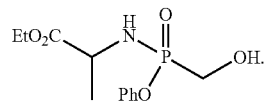 [SMILES: CCOC(=O)C(C)NP(=O)(CO)Oc1ccccc1]

In one embodiment the compound of formula 30 or 30b is not:

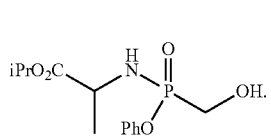

In one embodiment the compound of formula 31 or 31b is not:

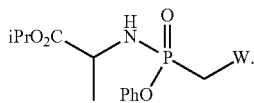

In cases where components identified herein are sufficiently basic or acidic to form stable acid or base salts, the invention also provides salts of such compounds. Such salts may be useful as intermediates, for example, for purifying such compounds. Examples of useful salts include those formed with organic acids, for example, tosylate, methanesulfonate, acetate, citrate, malonate, tartrate, succinate, benzoate, ascorbate, α-ketoglutarate, and α-glycerophosphate. Suitable inorganic salts may also be formed, including hydrochloride, sulfate, nitrate, bicarbonate, and carbonate salts.

Salts may be obtained using standard procedures well known in the art, for example by reacting a sufficiently basic compound such as an amine with a suitable acid affording an anion. Alkali metal (for example, sodium, potassium, or lithium) or alkaline earth metal (for example calcium or magnesium) salts of carboxylic acids, for example, can also be made.

Scheme 1 illustrates the method that was used to prepare the compound of formula 13 Scheme 2 illustrates a method that can be used to prepare other isomers of a compound of formula 13 (e.g. a compound of formula 13b) from the compound of formula 10a. Scheme 3 illustrates the method that was used to prepare the compound of formula 19. Scheme 4 illustrates a method that can be used to prepare other isomers of a compound of formula 19 (e.g. a compound of formula 19b). The compound of formula 19 was used as an intermediate to prepare the compound of formula 13 as described in Scheme 1. The synthetic methods used in the Schemes 1-4 are those methods described in the embodiments of the invention as described herein.

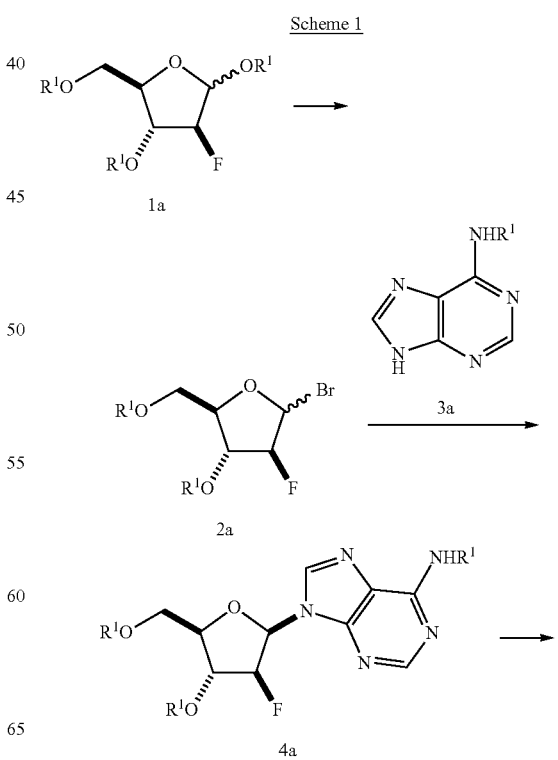

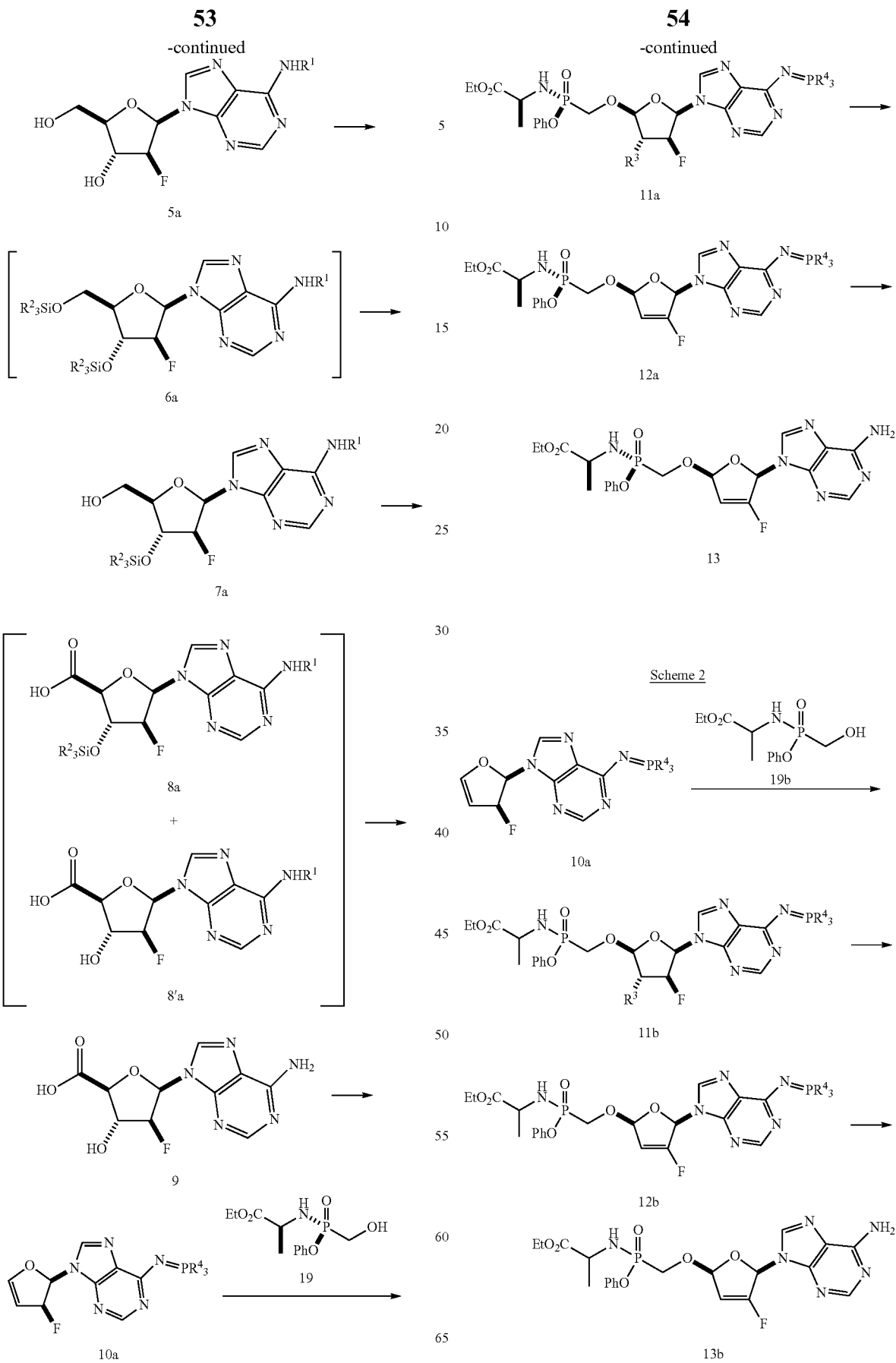

Scheme 3

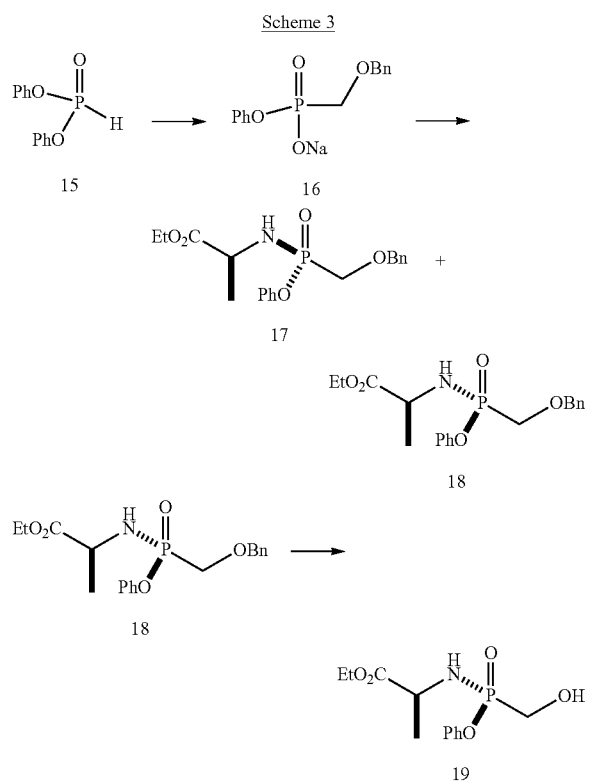

Scheme 4

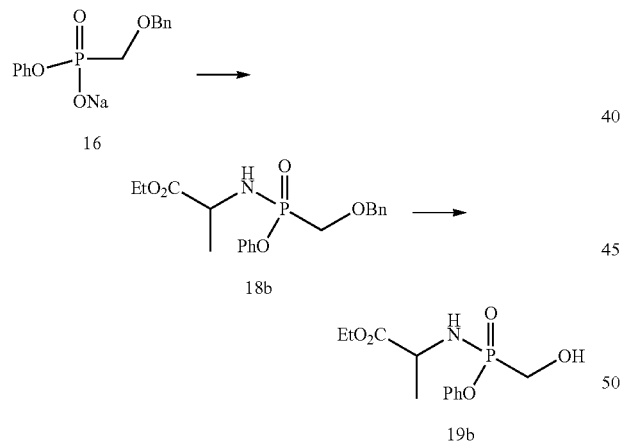

Scheme 5

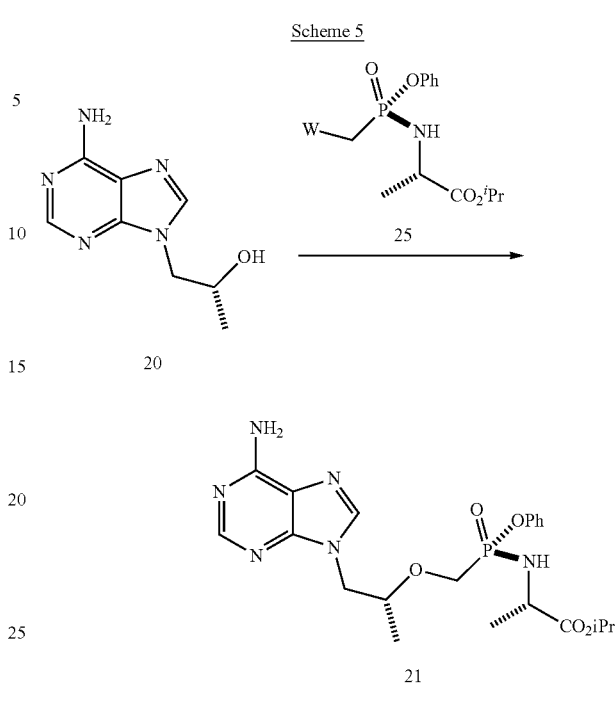

Scheme 6

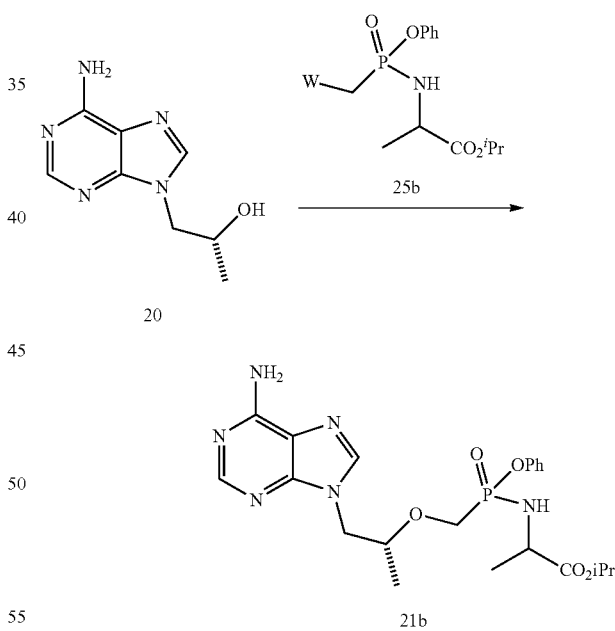

Scheme 5 illustrates a synthesis that can be used to prepare a compound of formula 21 from compound of formula 20. U.S. Pat. No. 7,390,791 describes the synthesis of compound 20. Scheme 6 illustrates a method that can be used to prepare other isomers of a compound of formula 21 (e.g. a compound of formula 21b) from the compound of formula 20. Scheme 7 illustrates a method that can be used to prepare the compound of formula 25. Scheme 8 illustrates a method that can be used to prepare other isomers of a compound of formula 24 (e.g. a compound of formula 25b). The compound of formula 25 can be used as an intermediate to prepare the compound of formula 21 as described in Scheme 5.

Scheme 7

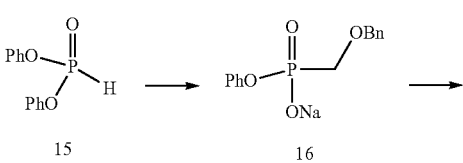

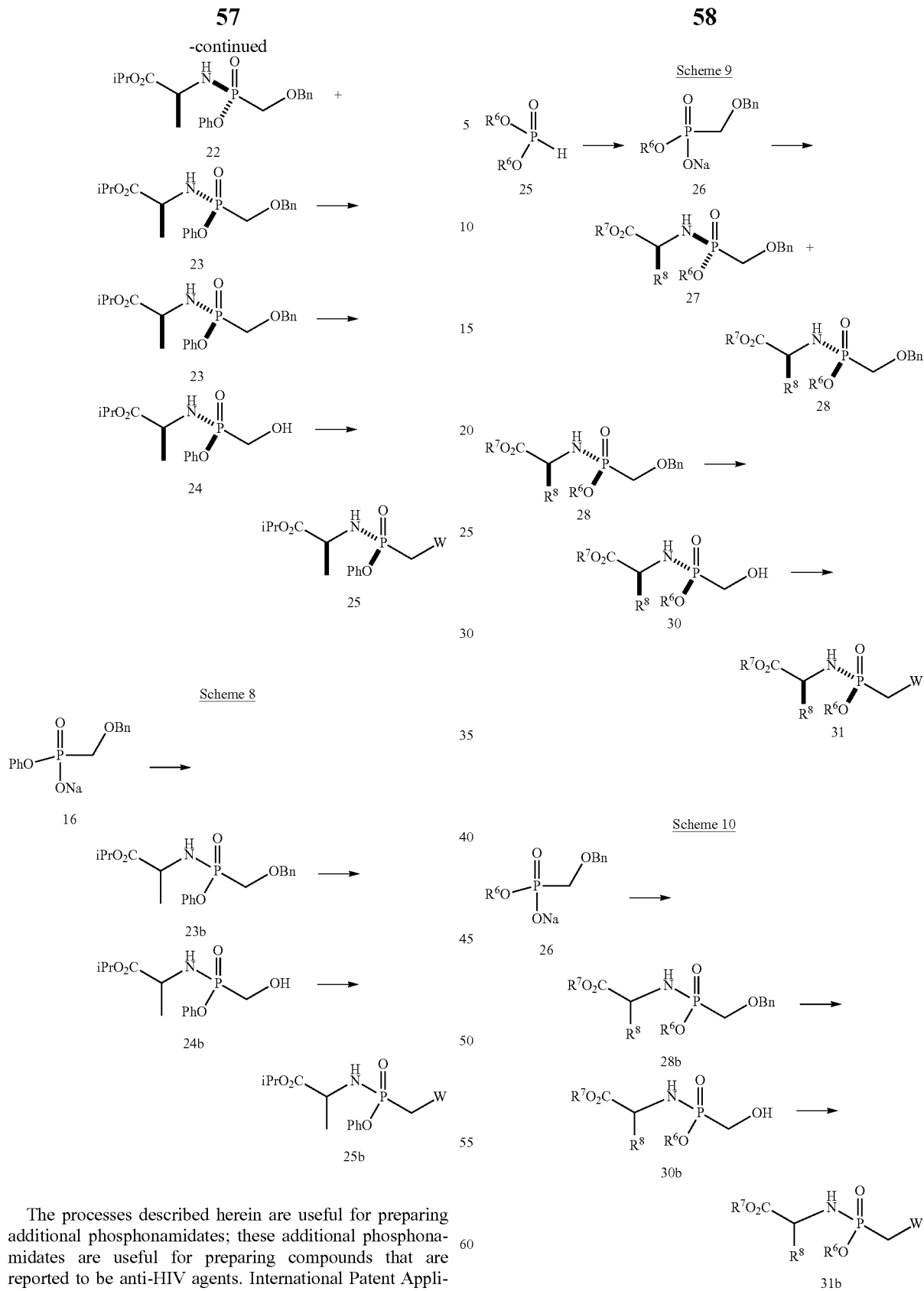

The processes described herein are useful for preparing additional phosphonamidates; these additional phosphonamidates are useful for preparing compounds that are reported to be anti-HIV agents. International Patent Application Publication Number WO 2006/110157 and International Patent Application Publication Number WO 2006/015261 describe such agents. Accordingly, the invention includes the novel phosphonamidates and processes illustrated in Schemes 9 and Scheme 10.

The invention also includes the processes and novel compounds of Schemes 11-13 which are useful for preparing compounds of formulas 13 and 13b.

Scheme 11
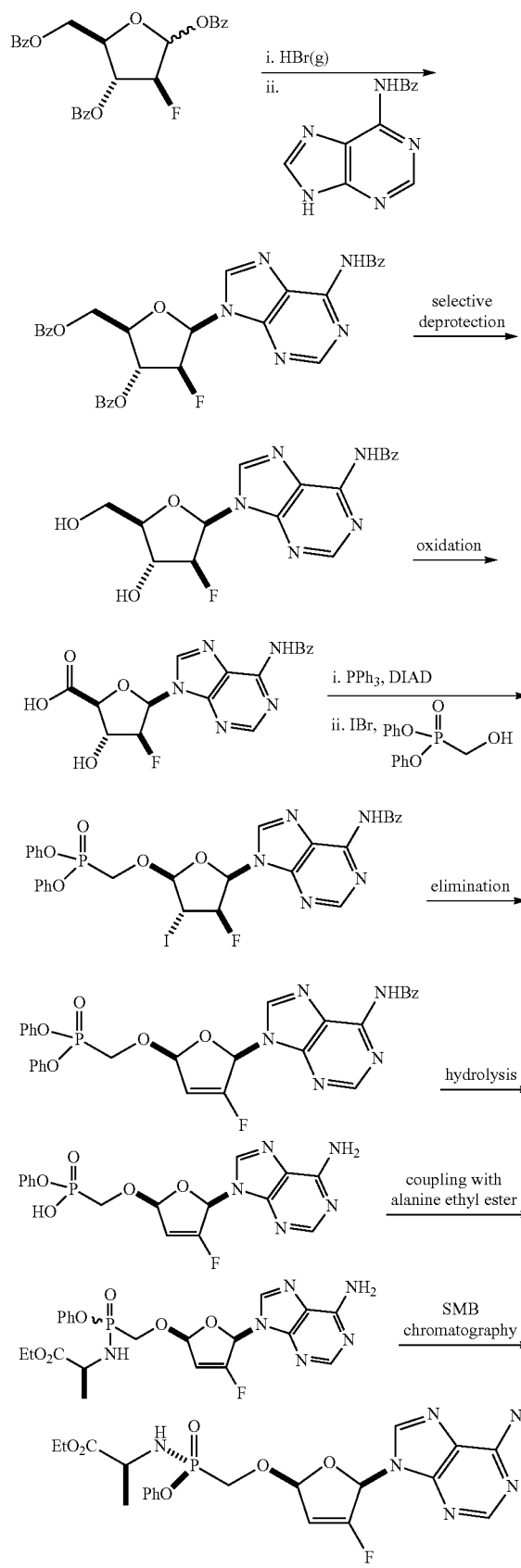
Scheme 12
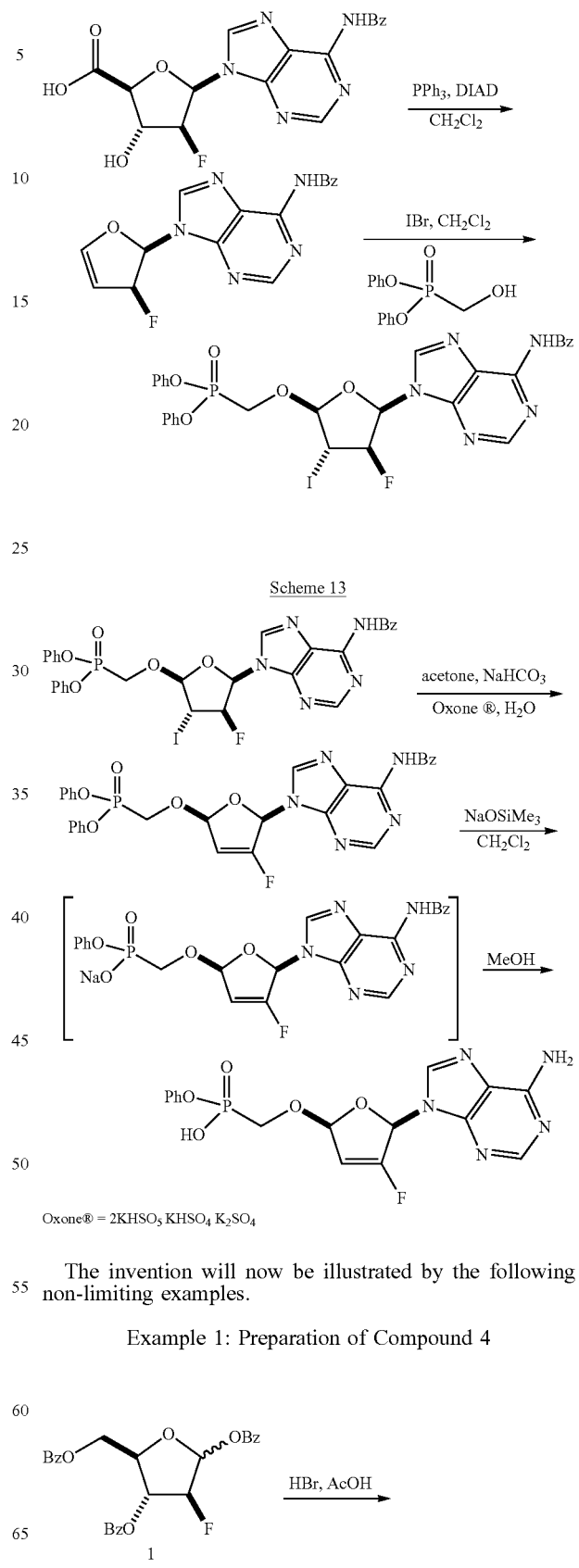
Scheme 13
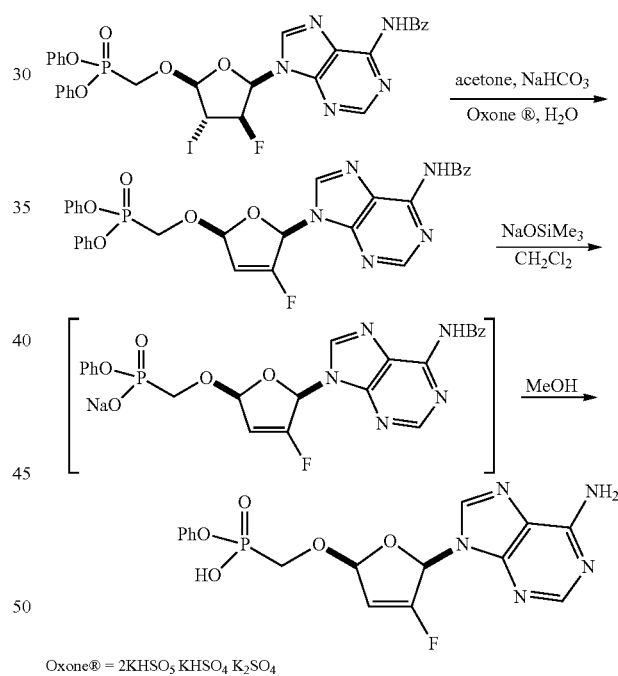
Oxone® = 2KHSO$_5$ KHSO$_4$ K$_2$SO$_4$
The invention will now be illustrated by the following non-limiting examples.
Example 1: Preparation of Compound 4
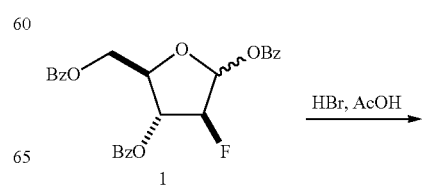

Example 2: Preparation of Compound 5

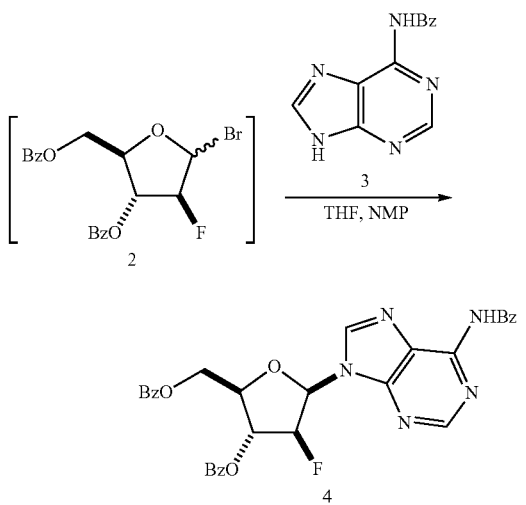

A reactor was charged with compound 1 (195 kg, 1.0 mole eq.) (U.S. Pat. No. 599,431; Tann, C. H. J. Org. Chem. 1985, 50, 3644-3647) and methylene chloride (936 kg). The contents were adjusted to ca. 0° C. A solution of HBr/HOAc (33 wt %) (410 kg, 4.0 mole eq.) was charged while maintaining the temperature at ca. 0° C. The contents were agitated at ca. 0° C. until the reaction was deemed complete by $^{19}$F NMR. The reaction mixture was washed with water (975 kg) twice at ca. 0° C. The organic layer was then washed with a 10 wt % $Na_2CO_3$ solution (975 kg). The organic layer was dried with $Na_2SO_4$ (97.5 kg) at ca. 22° C. for ca. 30 min and filtered and rinsed with methylene chloride (98 kg). The combined filtrates were concentrated to ~400 liters under reduced pressure at maximum jacket temperature of 40° C., followed by two co-distillations with tetrahydrofuran (585 kg each) to ~400 liters under reduced pressure at maximum jacket temperature 40° C. Tetrahydrofuran (2730 kg) was charged to the concentrate followed by compound 3 (222 kg, 2.2 mole eq.) (Rec. Trac. Chim Pays-Bas 105, 528-537, 1986), and NMP (98 kg). The content were agitated at reflux until the reaction was complete by $^{19}$F NMR. The reaction mixture was filtered and rinsed with tetrahydrofuran (195 kg). The filtrate and rinse were concentrated to ~400 liters under reduced pressure at maximum jacket temperature 40° C. Methylene chloride (975 kg) was charged to the reactor followed by a 3.5 wt % HCl solution (585 kg) and water (780 kg). The contents were agitated at ca. 22° C. for ~30 min. The separated organic layer was washed with water (585 kg) twice at ca. 22° C., then concentrated to ~400 liters under reduced pressure at maximum jacket temperature 40° C., followed by co-distillations with tetrahydrofuran (975 kg) twice to ~1,000 liters. The solution was discharged and the reactor rinsed with tetrahydrofuran (98 kg). Compound 4 was obtained as a tetrahydrofuran solution in 80% yield (196 kg) with an HPLC purity of 92.2% AN (3.9% α-anomer). $^1$H NMR (400 MHz, DMSO-d$_6$) δ11.3; (s, 1H), 8.8; (s, 1H), 8.6; (s, 1H), 8.2-8.0; (m, 6H), 7.8-7.4; (m, 9H), 6.8; (d, 1H), 6.0; (d, 1H), 5.9; (d, 1H), 4.6-4.9; (m, 3H).

Compound 4 (252 kg, 1 mole eq.) was charged to a reactor as a solution in tetrahydrofuran (1049 kg) and the temperature was adjusted to ca. 3° C. A 7.4 wt % aqueous solution of NaOH (1026 kg) was slowly charged to the reactor while maintaining the temperature at ca. 3° C. A sample of the reaction mixture was checked to ensure the pH was not less than 12. The reaction mixture was agitated at ca. 3° C. until the reaction was complete. Upon completion, the reaction mixture was washed with methyl tert-butylether (756 kg) at ca. 3° C. A 1N HCl solution (1260 kg) was slowly charged to adjust the pH to 6 to 7 while maintaining the temperature ca. 3° C. The mixture was adjusted to ca. 22° C. and tetrahydrofuran (3780 kg) was charged. After agitating the contents for 1 h, sodium chloride (756 kg) was charged and the aqueous layer was separated and extracted with tetrahydrofuran (1512 kg). The combined organic layers were concentrated at maximum jacket temperature of 40° C. to ~2500 liters. A sodium chloride solution (NaCl 479 kg; water 1436 kg) was charged while maintaining the temperature at ca. 40° C. After agitating for 30 min, the phases were separated and the organic layer was concentrated to ~500 liters at maximum jacket temperature of 45° C. The concentrate was co-evaporated with methanol (1260 kg) to ~500 liters at maximum jacket temperature of 45° C. until the THF content was NMT 5% by NMR. The mixture was adjusted to ca. 22° C. and agitated for ~4 h. After adjusting the temperature to ca. 3° C. and agitating for ~2 h, the slurry was filtered and rinsed with pre-cooled methanol (252 kg). The product was dried under vacuum at 45° C. Compound 5 was obtained in 64% yield (102.8 kg) with an HPLC purity of 97.6% AN. $^1$N NMR (400 MHz, DMSO-d$_6$) δ11.35; (brs, 1H), 8.77; (s, 1H), 8.61; (s, 1H), 8.04; (m, 2H), 7.63; (m, 1H), 7.54; (m, 2H), 6.58; (dd, J=4.8, 13.6 Hz, 1H), 6.05; (brs, 1H), 5.31; (ddd, J=4, 4, 52.4 Hz, 1H), 5.16; (brs, 1H), 4.50; (ddd, J=4.4, 4.4, 18.8 Hz, 1H), 3.90; (ddd, J=4.4, 4.4, 4.4 Hz, 1H), 3.69; (m, 2H). $^{19}$NMR (400 MHz, DMSO-d$_6$) δ −196.08; (ddd, J=14.4, 19.6, 54.8 Hz, 1F).

Example 3: Preparation of Compound 7

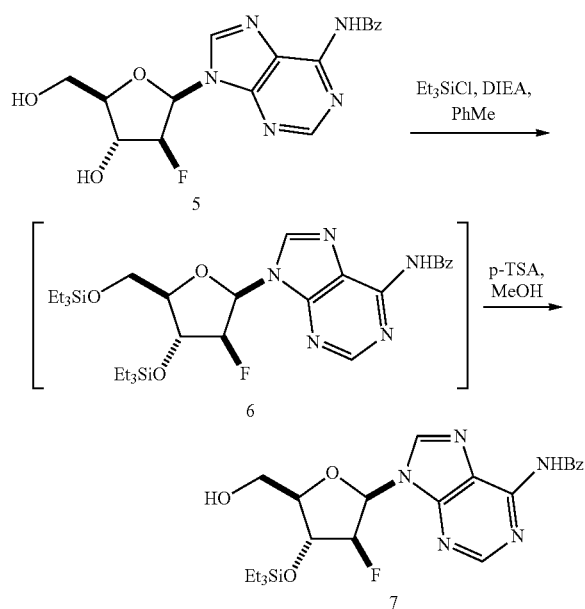

Compound 5 (79.5 kg, 1.0 mole eq.) was charged to a reactor and slurried in toluene (324 kg). Diisopropylethylamine (81 kg, 2.9 mole eq.) was then charged while the internal temperature was maintained at not more than 50° C. followed by a rinse with toluene (107 kg). Chlorotriethylsilane (84 kg, 2.9 mole eq.) was then charged while maintaining the internal temperature at not more than 50° C. followed by a rinse with toluene (16 kg). The reaction mixture was warmed to ca. 50° C. and agitated until the reaction was deemed complete. Upon completion, the reaction mixture was cooled to ca. 0° C. and filtered to remove diisopropylethylamine HCl salt, followed by a rinse with toluene (162 kg). The filtrate was concentrated to ca. 250 liters to remove residual diisopropylethylamine. The product rich toluene solution was cooled to ca. 0° C. and a solution of p-toluenesulfonic acid monohydrate (5.7 kg, 0.13 mole eq.) in methanol (1130 kg) was slowly charged while the reaction temperature was maintained at ca. 0° C., followed by a rinse with methanol (81 kg). The resulting solution was agitated at ca. 0° C. until the reaction was deemed complete. Once complete, the reaction mixture was quenched with 0.5% sodium bicarbonate solution (811 kg), followed by the addition of methylene chloride (564 kg). The organic layer was separated and the aqueous layer was extracted with methylene chloride (564 kg) twice. The organic layers were combined and solvent exchanged to isopropyl acetate. After being concentrated to ~240 liters, the resulting slurry was cooled to ca. 0° C. and agitated at that temperature for ~2 h then filtered, followed by a rinse with isopropyl acetate (79.5 kg). The solid product, compound 7, was dried under vacuum at a maximum temperature of 40° C. Compound 7 was obtained in 77.8% yield (81 kg) with an HPLC purity of 94% AN. $^1$H NMR (400 MHz, CDCl$_3$) δ9.35; (brs, 1H), 8.82; (s, 1H), 8.22; (d, J=2 Hz, 1H), 8.03; (m, 2H), 7.60; (m, 1H), 7.52; (m, 2H), 6.51; (dd, J=4, 17.2 Hz, 1H), 5.07; (ddd, J=2.4, 4, 52 Hz, 1H), 4.66; (ddd, J=2.4, 4, 17.6 Hz, 1H), 4.03; (ddd, J=4, 4, 4 Hz, 1H), 3.78; (m, 1H), 3.86; (m, 1H), 3.94; (m, 1H), 0.97; (t, J=8 Hz, 9H), 0.66; (q, J=8 Hz, 6H). $^{19}$F NMR (400 MHz, DMSO-d$_6$) δ −195.19; (ddd, J=18.5, 18.5 56.0, 1F).

Example 4: Preparation of Compound 9

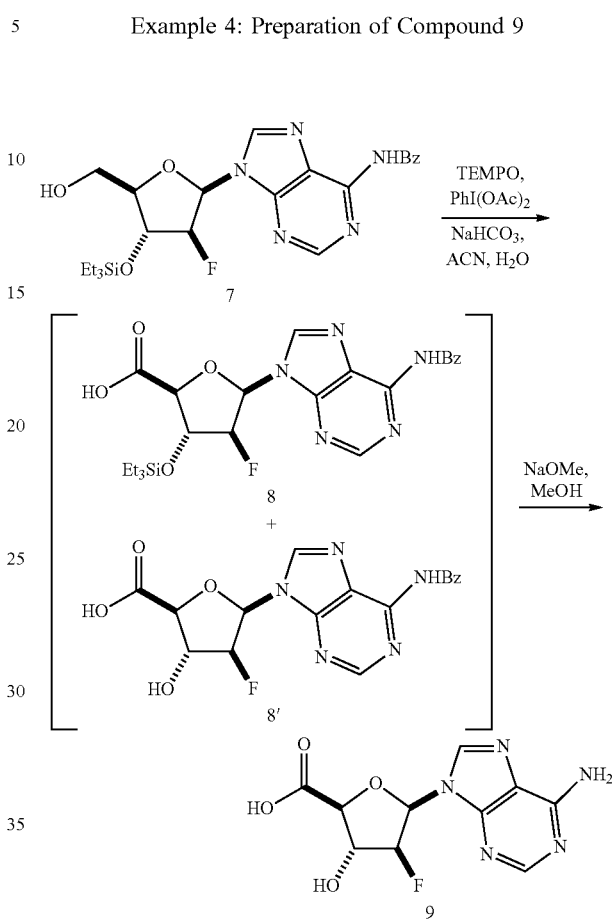

Compound 7 (86.4 kg, 1.0 mole eq.) was charged to a reactor followed by the addition of acetonitrile (778 kg). The contents were adjusted to 40° C. and agitated for ~15 min, then adjusted to 22° C. Water (778 kg), NaHCO$_3$ (104 kg), and TEMPO (9.5 kg, 034 mol eq.) were charged to the reactor ensuring the pH is not less than 8. Diacetoxyiodobenzene (173 kg, 3.03 mol eq.) was charged to the reactor in ~10 equal portions while maintaining the temperature at ca. 22° C., the reaction mixture was agitated for ~15 min between each portion. As needed, 30% acetic acid was added to maintain the pH at 6.5 to 7.0. 1 N NaHCO$_3$ solution was added to back adjust the pH as needed. The reaction mixture was agitated at ca. 22° C. until the reaction was deemed complete. Upon completion, a 10% sodium sulfite solution (104 kg) was charged maintaining the internal temperature at ca. 22° C. and agitated for ~15 min. A KI paper test was conducted; if a positive test result, additional 10% sodium sulfite solution (26 kg) was charged. 2-Methyltetrahydrofuran (691 kg) and water (259 kg) were charged to extract the intermediate compound 8. The separated aqueous was extracted with 2-methyltetrahydrofuran (302 kg). 12 N HCl solution (101 kg) was slowly charged to the aqueous layer at ca. 22° C. to adjust the pH to 3.0 to 3.5, followed by addition of sodium chloride (86 kg) and tetrahydrofuran (346 kg) to extract the intermediated compound 8'. The aqueous layer was extracted with tetrahydrofuran (346 kg). The combined organic solutions were charged to a reactor, followed by NaHCO₃ (138 kg). The mixture was agitated at ca. 22° C. for 1 h, and concentrated to ca. 170 liters at maximum jacket temperature of 60° C. The concentrate was then co-evaporated with toluene (432 kg) three times. Toluene (432 kg) was charged to the resulting residue and an in-process KF analysis was conducted (KF NMT 0.5%), the mixture was then concentrated to ca. 170 liters at maximum jacket temperature of 60° C. Methanol (437 kg and 86 kg) and a 25% NaOMe solution in methanol (82 kg) were charged to the reactor, and the reaction mixture was agitated at ca. 22° C. until the reaction was complete. Upon completion of the reaction, the reaction mixture was adjusted to ca. 10° C. and a 6 N HCl solution was slowly charged to adjust the pH to 3.0 (2.8 to 3.2) while maintaining the temperature at NMT 25° C. Water (173 kg) was charged while maintaining the temperature at NMT 25° C. The contents were adjusted to ca. 22° C. and agitated at the temperature for ~2 h. The slurry was filtered and rinsed with water (86 kg) twice and tetrahydrofuran (43 kg) twice. The product (compound 9) was dried at maximum jacket temperature of 60° C. until KF was not more than 1.0%. Compound 9 was obtained in 71.8% yield (33.8 kg) with an HPLC purity of 98.2% AN. ¹H NMR (400 MHz, DMSO-d₆) δ8.37; (s, 1H), 8.14; (s, 1H), 7.38; (s, 2H), 6.53; (d, ³J$_{H-F}$ 23.2 Hz, 1H). 5.07; (d, ²J$_{H-F}$ 50.8 Hz, 1H), 4.63; (d, ³J$_{H-F}$ 9.99 Hz, 1H), 4.54; (s, 1H). ¹⁹F NMR (400 MHz, DMSO-d₆) δ −198.19; (m, 1F).

Example 5: Preparation of Compound 10

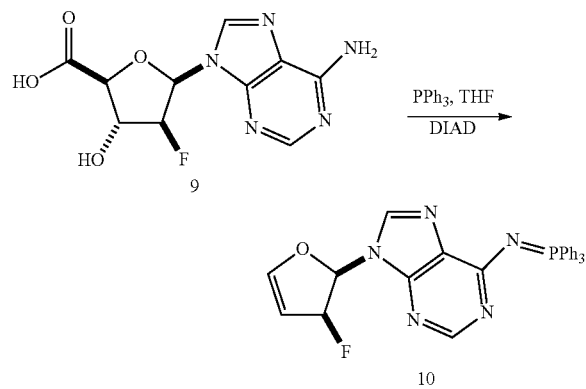

Compound 9 (30 kg, 1.0 mole eq.) was charged to a reactor followed by triphenylphosphine (90 kg, 3.3 mole eq.) and the solids were slurried in tetrahydrofuran (150 kg). Diisopropyl azodicarboxylate (72 kg, 3.4 mole eq.) was slowly charged to the slurry over a minimum of 120 min and maintaining the reaction temperature not more than 35° C. After the addition was complete, the lines were rinsed with tetrahydrofuran (15 kg). The contents were agitated for ca. 12 h at 22° C. until the reaction was deemed complete by ¹⁹F NMR. The reaction mixture was filtered through a polishing filter into another reactor followed by a rinse with tetrahydrofuran (30 kg). The filtered reaction mixture was cooled to ca. −22° C. Methyl tert-butylether (150 kg) was charged over a minimum of 1 h and then heptanes (600 kg) over a minimum of 8 h, maintaining a maximum of −22° C. The resultant slurry was then agitated for ca. 10 h at −10° C. and filtered. The filter cake was rinsed with two portions of cold (−10° C.) methyl tert-butylether (60 kg) each. The wet cake was transferred to the reactor and reslurried in methyl tert-butylether (3000 kg), at ca. 35° C. for ca. 20 h. The reaction mixture was adjusted to 18° C., and then agitated for a minimum of 3 h. The slurry was filtered and rinsed with two portions of methyl tert-butylether (60 kg). Before drying, a sample of filter cake was obtained for DIAD-H₂ and TPPO contents (TPPO by ³¹P NMR≤8%, DIAD-H₂ by ¹H NMR). If necessary, the methyl tert-butylether reslurry was repeated. The product (compound 10) was dried under vacuum at maximum 40° C. Compound 10 was obtained in 77% yield (39.4 kg, corrected for purity and MTBE contents by NMR analysis). ¹H NMR (400 MHz, DMSO-d₆) δ8.05; (d, J=3.2 Hz, 1H), 7.99; (s, 1H), 7.89-7.79; (m, 6H), 7.66-7.52; (m, 9H), 7.24; (s, 1H), 6.72; (dd, J$_{H-H}$ 5.6 Hz, ³J$_{H-F}$ 28.4 Hz, 1H), 5.80; (dd, J$_{H-H}$ 3.6 Hz, ²J$_{H-F}$ 59.9 Hz, 1H), 5.62; (s, 1H). ¹⁹F NMR (400 MHz, DMSO-d₆) δ −167.88; (dd, ³J$_{H-F}$ 28.6 Hz, ²J$_{H-F}$ 59.4 Hz, 1F). ³¹P NMR (400 MHz, DMSO-d₆) δ17.36 (s, 1P).

Example 6: Preparation of Compound 11

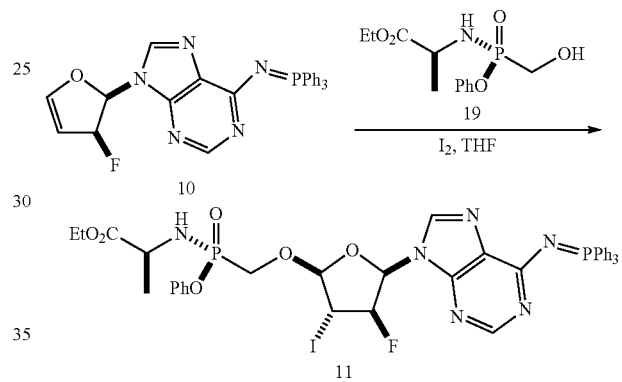

Iodine (165 kg, 8.0 mole eq.) and tetrahydrofuran (236 kg) were charged to a reactor. The mixture was agitated for ca. 1 h at ca. 22° C. followed by addition of 4 Å molecular sieves (9.9 kg). The contents were adjusted to ca. −12° C., and compound 19 (26.0 kg, 1.1 mole eq.) and tetrahydrofuran (39 kg) were charged. Compound 10 (38.8 kg, corrected for purity, 1.0 mole eq.) was added at ca. −12° C. (Note: the addition is mildly exothermic; the first portion should be less than 10% of the total weight), followed by tetrahydrofuran (39 kg). The contents were agitated for ca. 18 h at ca. −12° C. then at ca. 22° C. until the reaction was complete. The reaction mixture was filtered and the reactor rinsed with two portions of tetrahydrofuran (79 kg). Methylene chloride (197 kg) was charged to the filtrate and the temperature was adjusted to ca. −15° C., followed by addition of a solution of sodium sulfite (197 kg) in water (1036 kg) (For the first ca. 50% of the addition, the internal temperature was maintained at NMT 0° C. For the remainder of the addition, the internal temperature was kept at not more than 10° C.; the addition of the first 20% is very exothermic). After adjusting the internal temperature to ca. 15° C., a sample was taken to confirm the pH is 6 to 7. Toluene (1180 kg) was charged and the layers were separated. The organic layer was concentrated to a volume of ca. 250 liters at maximum jacket temperature 40° C. Methylene chloride (39 kg) was charged and the content adjusted to ca. 30° C. and agitated until a clear solution was achieved. The solution was slowly charged to heptane (985 kg) that was pre-cooled to ca. 0° C. over a minimum of 30 min. The resultant slurry was agitated for 2 h and then filtered and rinsed with two portions of heptane (79 kg). The filter cake was dried at maximum internal temperature of 35° C. Compound 11 was obtained in 81% yield (58.5 kg, corrected for purity and LOD) with an HPLC purity of 80.9% AN. $^1$H NMR (400 MHz, DMSO-d$_6$) δ8.12; (s, 1H), 8.07; (d, J=3.2 Hz, 1H), 7.86-7.89; (m, 6H), 7.51-7.55; (m, 3H), 7.41-7.44; (m, 6H), 7.23-7.35; (m, 5H), 7.18-7.20; (m, 2H), 7.04; (dd, J=3.6, 19.5 Hz, 1H), 5.53; (s, 1H), 5.35; (dd, J=4.0, 52.8 Hz, 1H), 4.10-4.25; (m, 3H), 3.92; (t, J=10.8, 1H), 3.87; (dd, J=10.4, 13.6 Hz, 1H), 1.22-1.29; (m, 6H). $^{19}$F NMR (400 MHz, DMSO-d$_6$) δ −163.93; (dddd, J=4.0, 20.8, 20.8, 56.4 Hz, 1F). $^{31}$P NMR (400 MHz, DMSO-d$_6$) δ18.4; (s, 1P), 19.1; (s, 1P).

Example 7: Preparation of Compound 12

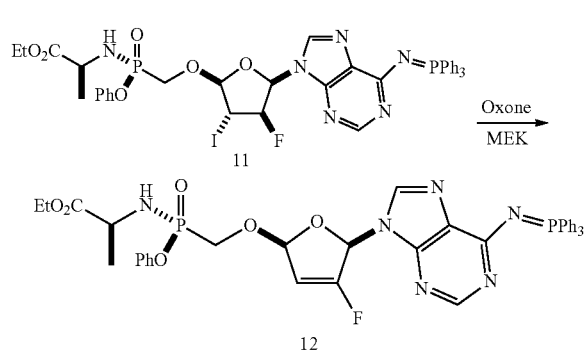

Compound 11 (42 kg, corrected for LOD, 1.0 mole eq.) was charged to a reactor followed by 2-butanone (504 kg) and a sodium phosphate buffer solution [NaH$_2$PO$_4$.H$_2$O (4.6 kg), Na$_2$HPO$_4$ (22 kg and water (420 kg)]. A 20% potassium peroxymonosulfate (2310 kg, 20 mole eq.) solution and 10% sodium hydroxide solution (882 kg) were charged simultaneously to the reaction mixture, for a minimum of 4 h, at 20° C. maintaining a pH range of 6.0 to 7.0. During the reaction, the pH should be adjusted with the 10% sodium hydroxide solution to maintain a pH of 6.0 to 7.0. After the reaction was deemed complete, water (630 kg) and ethyl acetate (420 kg) were added. The contents were cooled to ca. 10° C. and a mixture of sodium metabisulfite (101 kg) and sodium sulfite (46 kg) in water (265 L) were charged over a minimum of 1 h, maintaining a temperature range ca. 10° C. and a pH range (6.5-8.0). The mixture was agitated for a minimum of 10 min, then the absence of oxidant was confirmed with wet KI paper (the sample is acidified with 1 N HCl until pH≤2). Water (420 kg) was charged and the contents were warmed to ca. 20° C. The phases were separated and the aqueous layer was extracted with ethyl acetate (420 kg). The combined organic layers were washed with brine [sodium chloride (21 kg) water (84 kg)] then the layers were separated. The organic layer was concentrated to ca. 200 liters at maximum temperature of 40° C. The concentrate was co-evaporated with ethyl acetate (420 kg) until the KF≤0.5%. The concentrate was filtered through a polished filter followed by a rinse with ethyl acetate (84 kg). The product rich ethyl acetate concentrate was added to a mixture of methyl tert-butylether (210 kg) and n-heptane (1500 kg) over a minimum of 1 h and the resultant slurry was agitated for a minimum of 1 h at ca. 20° C. The slurry was cooled to ca. −10° C. over 2 h and agitated for at least 1 h. The contents were filtered and filter cake was rinsed with two portions of cold (−15 to −5° C.) n-heptane (200 kg). The product (compound 12), was dried under vacuum at maximum 30° C. Compound 12 was obtained in 62% yield (22 kg) with an HPLC purity of 72% AN. $^1$H NMR (400 MHz, DMSO-d$_6$) δ8.12; (s, 1H), 8.04; (s, 1h), 7.93-7.87; (m, 3H), 7.55-7.51; (m, 3H), 7.46-7.42; (m, 6H), 7.24-7.20; (m, 3H), 7.15-7.13; (m, 2H), 7.06; (t, J=7.6 Hz, 1H), 6.76; (d, J=2.8 Hz, 1H), 5.83; (d, J=4.0 Hz, 1H), 5.72; (s, 1H), 4.21-4.11; (m, 3H), 3.91; (dd, J=9.2, 14.0 Hz, 1H), 3.67; (t, J=10.8 Hz, 1H), 1.33 (d, J=7.2 Hz, 3H), 1.24; (t, J=7.2 Hz, 3H). $^{19}$F NMR (400 MHz, DMSO-d$_6$) δ −130.13; (br, s, 1F). $^{31}$P NMR (400 MHz, DMSO-d$_6$) δ19.96; (s, 1P), 17.89; (s, 1P).

Example 8: Preparation of Compound 13

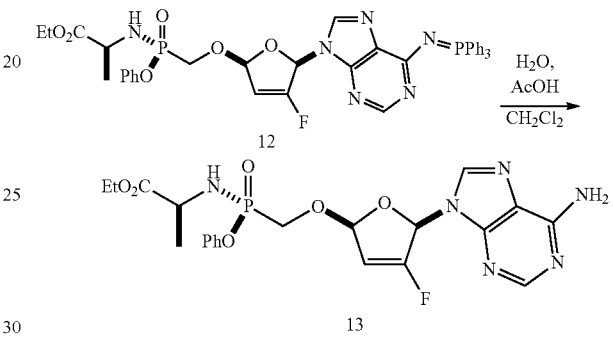

Compound 12 (22 kg, 1.0 mole eq.) was charged to a reactor and dissolved in methylene chloride (66 kg). The contents were agitated at an internal temperature of 20° C. Acetic acid (11 kg) was charged to the solution at a rate to maintain the internal temperature of not more than 25° C. Water (5.5 kg) was then charged to the reaction. The reaction was agitated at ca. 22° C. until not more than 5% of compound 12 remained by HPLC. Upon completion, the internal temperature was cooled to ca. 3° C. A 7.7 weight % sodium bicarbonate solution [NaHCO$_3$ (20 kg), water (242 kg)] was charged until a pH value of ca. 7.0 was achieved maintaining a maximum temperature of ca. 10° C. Methylene chloride (88 kg), methyl tert-butylether (44 kg) and water (110 kg) were added and the mixture was agitated at a maximum temperature of 6° C. The phases were separated and the aqueous layer was extracted twice with a mixture of methylene chloride (110 kg) and methyl tert-butylether (44 kg), then once with a mixture of methylene chloride (25 kg) and methyl tert-butylether (18 kg) at a maximum temperature of 6° C. The organic layers were combined, and dried over magnesium sulfate (22 kg) until a KF value of NMT 0.3% is achieved. The mixture was filtered and the filtrate was concentrated under vacuum. The resultant concentrate was purified by silica gel (165 kg) column chromatography. The column was conditioned with methylene chloride and the product rich concentrate was eluted with a mixture of methanol and ethyl acetate. The fractions were collected and concentrated under vacuum with a maximum jacket temperature of 30° C. The resultant compound 13 solution was stored at frozen conditions. The solution contained compound 13 in 54% yield (7.7 kg) with an HPLC purity of 95% AN. $^1$H NMR (400 MHz, DMSO-d$_6$) δ8.21; (s, 1H), 8.20; (s, 1H), 7.46; (br, 1H), 7.32-7.28; (m, 2H), 7.16-7.10; (m, 3H), 6.87; (d, J=2.4 Hz, 1H), 6.15; (s, 1H), 5.97; (d, J=4.0 Hz, 1H), 5.81; (dd, J=10.0, 12.0 Hz, 1H), 4.07-3.83; (m, 5H), 1.14; (t, J=8 Hz, 3H), 1.12; (t, J=6.8 Hz, 3H). $^{19}$F NMR (400 MHz, DMSO-d$_6$) δ −131.62 (s, 1F). $^{31}$P NMR (400 MHz, DMSO-d$_6$) δ21.68; (s, 1P).

Example 9. Preparation of Benzyloxymethylphosphonic Acid, Monophenyl Ester, Monosodium Salt (Compound 16)

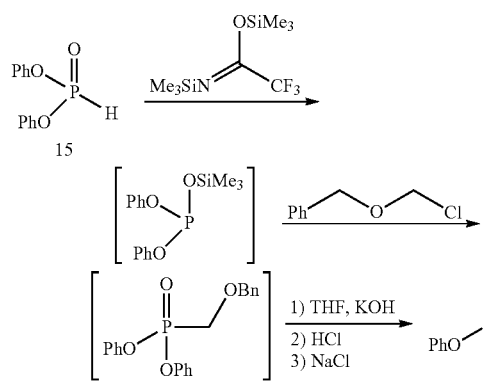

Diphenyl phosphite 15 (406.7 kg, 1 mole eq.) was charged to a reactor. The internal temperature was adjusted to 32 to 38° C., followed by the addition of bis(trimethylsily)trifluoroacetamide (BSTFA) (459 kg, 1.03 mole eq.) while maintaining the internal temperature within this range. The resulting mixture was agitated at this temperature until complete by $^{31}$P NMR (normally 1 to 3 h). Upon reaction completion, benzyl chloromethyl ether (BOMCl) (327 kg, 1.17 mole eq.) was charged and the reaction mixture was heated to ca. 75° C. and agitated until complete by $^{31}$P NMR. Once complete, the reaction mixture was cooled to ca. 22° C. and tetrahydrofuran (731 kg) was added. The mixture was then quenched with water (3289 kg) while the temperature was maintained below 40° C. (exotherm was observed). The temperature was then adjusted to ca. 22° C. and 45% w/w KOH solution (1289 kg) was added and the mixture was agitated at ca. 22° C. until the reaction was judged complete by TLC (typically 10 to 14 h). The organic layer was removed and the pH of the aqueous layer was adjusted to 6.8 to 7.2 with concentrated HCl. The neutral aqueous layer was washed with ethyl acetate (1462 kg) at the temperature range of 40 to 46° C. The ethyl acetate layer was charged with heptane (154 kg) and the resulting mixture was back extracted with water (548 kg) at the temperature range of 40 to 46° C. The aqueous layers were combined and washed twice with a mixture of heptane (406 kg) and ethyl acetate (544 kg) at the temperature range of 40 to 46° C. The aqueous layer was concentrated under vacuum to ca. 5000 liters with the jacket temperature set at a maximum 65° C. Water (812 kg) was charged, followed by portion-wise addition of sodium chloride (844 kg) while the pot temperature was maintained at the range between 62 and 68° C. A thick slurry was formed and the pot temperature was slowly adjusted to ca. 3° C. over a period of 4 h. After being agitated at ca. 3° C. for ca. 2 h, the product was filtered cold and rinsed first with a cold (2 to 8° C.) brine solution (20 kg NaCl in 146 kg water), then heptane (ca. 700 kg). After being dried in oven under vacuum at ca. 70° C., compound 16, was obtained in 82% yield (427.5 kg, corrected for HPLC purity and KF) as a white solid with an HPLC purity of 98.9% AN. $^1$H NMR (400 MHz, CDCl$_3$) δ7.4-6.9; (m, 10H), 4.49; (s, 2H), 3.72; (d, J=8.8 Hz, 2H). $^{31}$P NMR (400 MHz, CDCl$_3$) δ18.74; (s, 1P).

Example 10: Preparation of N-(benzyloxymethyl-phenoxyphosphinylidene)-L-alanine ethyl ester (Compound 17 and Compound 18)

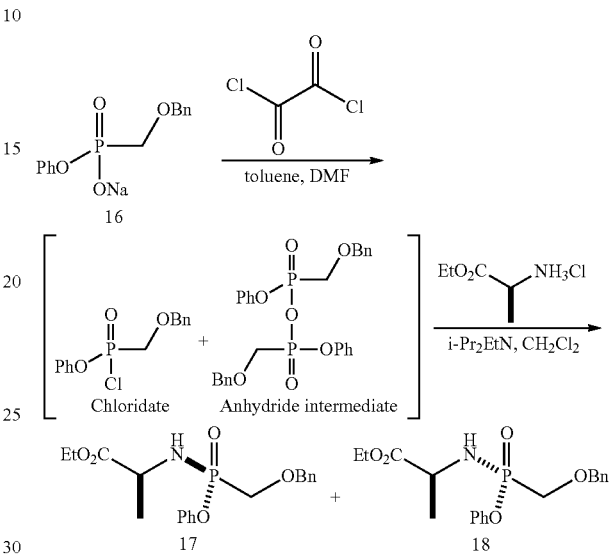

Compound 16 (216.8 kg, 1.0 mole eq.), was charged to a reactor, followed by N—N-dimethylformamide (11 kg) and toluene (1037 kg). The temperature was adjusted to 0 to 6° C., followed by the slow addition of a solution of oxalyl chloride (108 kg, 1.18 mole eq.) in toluene (216 kg) over a minimum period of 4 h while the temperature was maintained at maximum 15° C. The reactor was rinsed forward with toluene (65 kg). The temperature was adjusted to 37 to 43° C. and the mixture was agitated at this temperature until the reaction was judged complete by $^{31}$P NMR. Once the reaction was complete, the temperature was adjusted to 19 to 25° C. and the sodium chloride by-product was filtered, followed by a rinse with toluene (216.8 kg). The filtrate containing the desired intermediate was concentrated under vacuum to dryness and co-evaporated twice with toluene (432 kg) to remove residual oxalyl chloride with a maximum jacket temperature of 60° C. A previously dried (with sodium sulfate) solution of L-alanine ethyl ester HCl (126 kg, 1.11 mole eq.) in methylene chloride (1306 kg) was added to the product rich toluene concentrate at 19 to 25° C. and the temperature of the resulting mixture was adjusted to 7 to 13° C. Diisopropylethylamine (212 kg, 2.28 mole eq.) was slowly added to the reaction mixture while the temperature was maintained at not more than 25° C. Once the addition was complete, the reaction mixture was adjusted to 19 to 25° C. and agitated until the reaction was judged complete by $^{31}$P NMR. The reaction mixture was washed twice with a KH$_2$PO$_4$/NaOH, 0.05M (pH 7) buffer solution (432 kg) and the organic layer was dried over sodium sulfate (86 kg). Sodium sulfate was filtered and the filter cake was washed with methylene chloride (108.4 kg). The filtrate was then treated with silica gel (130 kg) in heptane (907 kg) at 19 to 25° C. The silica gel was filtered and rinsed with two portions of a mixture of methylene chloride (216 kg) and heptane (151 kg). The combined filtrates were concentrated to dryness under vacuum with a maximum jacket temperature of 60° C., followed by a co-evaporation with absolute ethanol (648 kg). Absolute ethanol (216 kg) was charged to the concentrate and the mixture was agitated until a homogeneous solution was obtained. The concentration of the product solution was adjusted to ~50 weight % for the subsequent SMB separation. The product (mixture of compounds 17 and 18) was obtained as an ethanolic solution in 87% yield (237.6 kg) with an HPLC purity of 87.8% AN. $^1$N NMR (400 MHz, CDCl$_3$) δ7.4-7.1; (m, 10H), 4.7-4.4; (m, 2H), 4.2-3.9; (m, 3H), 3.9-3.6; (m, 3H), 1.4-1.2; (m, 6H). $^{31}$P NMR (400 MHz, CDCl$_3$) δ23.72; (s, 1P, 22.78; (s, 1P).

Example 11: Resolution of Compound 18

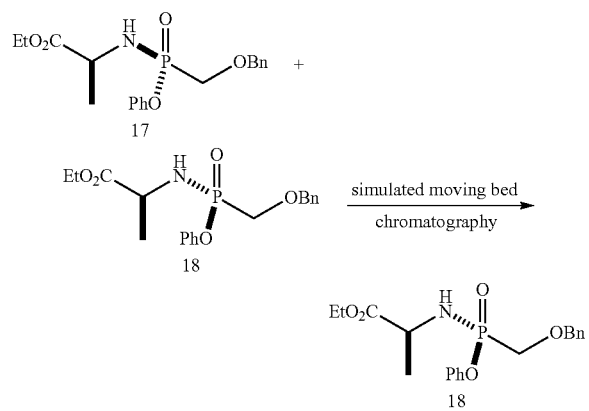

The resolution was performed on Chiralpak AS with an ethanol and heptane mobile phase using simulated moving bed (SMB) chromatography. The mixture of compound 17 and compound 18 (238 kg) was resolved to provide compound 18 as an ethanolic solution (104 kg of compound 18) in a 44% yield with an HPLC purity of 98.1% AN and a de of 99.8%. $^1$H NMR (400 MHz, CDCl$_3$) δ7.5-7.1; (m, 10H), 4.64; (s, 2H), 4.3-4.0; (m, 3H), 3.9-3.7; (m, 2H), 3.7-3.5; (m, 1H), 1.29; (d, J=6.8 Hz, 3H), 1.22; (t, J=7.2 Hz, 3H). $^{31}$P NMR (400 MHz, CDCl$_3$) δ22.74; (s, 1P).

Example 12: Preparation of Compound 19

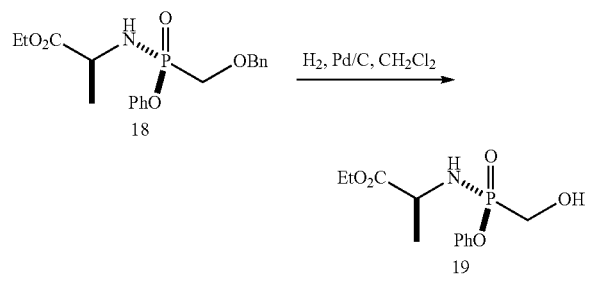

Compound 18 (103 kg, 1.0 mole eq.) as an ethanolic solution (254 kg) was charged to a reactor followed by the addition of methylene chloride (311 kg). Water (208 kg) was charged, maintaining a maximum temperature of 25° C. (addition is exothermic). The reactor contents were adjusted to 22° C. followed by phase separation. The organic layer was washed with water (208 kg) one more time at 22° C. Methylene chloride (208 kg) was charged to the organic layer. The resulting solution was hydrogenated at a maximum temperature of ca. 22° C. using ca. 50 psi hydrogen with agitation in the presence of 10% Pd/C (10.4 kg), until NMT 1% of compound 18 remained by HPLC % AN. The reaction mixture was adjusted to ca. 0° C. and the catalyst was removed by filtration, rinsing with cold methylene chloride (146 kg) twice. The filtrate was washed with water (208 kg) maintaining a maximum temperature of ca. 13° C. The organic layer was concentrated under vacuum to ca. 104 liters and methyl tert-butylether (520 kg) was charged to the concentrate. The reactor contents were concentrate to ca. 416 L. Methyl tert-butylether (312 kg) was charged to the concentrate. The reactor contents were concentrated to ca. 520 L, yielding a slurry. The slurry was adjusted to ca. −20° C. and agitated at that temperature for a minimum of 3 h. The product was filtered and rinsed with cold MTBE (70 kg). The product was dried under vacuum until an LOD value of maximum 1% was achieved. Compound 19 was obtained in 83% yield (64.8 kg) with an HPLC purity of 99.8% AN and a de of 99.8% and stored at refrigerated conditions. $^1$H NMR (400 MHz, DMSO-d$_6$) δ7.36-7.32; (m, 2H), 7.21-7.13; (m, 3H), 5.55-5.49; (dd, J=12.0, 10.4 Hz, 1H), 5.37; (dt, J=11.6, 6.0, 6.0 Hz, 1H), 4.02; (ddd, J=14, 7.2, 2.0 Hz, 1H), 3.91; (ddd, J=14, 7.2, 2.4 Hz, 1H), 3.75; (t, J=6.4, 2H), 1.19; (d, J=7.2 Hz, 3H), 1.14; (t, J=7.2, 3H). $^{31}$P NMR (400 MHz, CDCl$_3$) δ25.86; (s, 1P).

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A method of preparing a compound of formula 14:

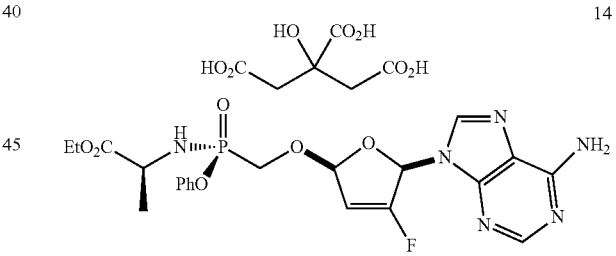

comprising:
(a) converting a compound of formula 12a:

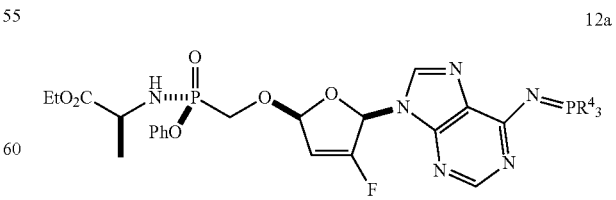

to a compound of formula 13, wherein each R$^4$ is independently (C$_1$-C$_6$)alkyl, (C$_3$-C$_7$)cycloalkyl, or (C$_3$-C$_7$)aryl, and wherein any (C$_3$-C$_7$)cycloalkyl or (C$_3$-C$_7$)aryl is unsubstituted or substituted with up to five (C$_1$-C$_6$)alkyl groups, wherein the compound of formula 12a is treated with a deprotecting agent to give a compound of formula 13; and (b) converting the compound of formula 13

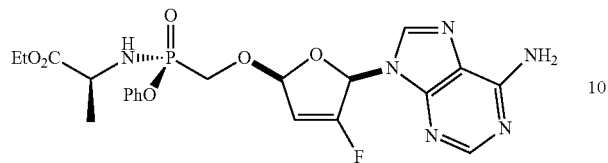

13 to the compound of formula 14, wherein the compound of formula 13 is treated with citric acid.

2. The method of claim 1, wherein each $R^4$ is phenyl.

3. The method of claim 1, wherein the deprotecting agent is an acid.

4. The method of claim 3, wherein the acid is acetic acid.

5. The method of claim 3, wherein the acid is trifluoroacetic acid.

* * * * *